US007566742B2

(12) United States Patent
Silcock et al.

(10) Patent No.: US 7,566,742 B2
(45) Date of Patent: Jul. 28, 2009

(54) PHOSPHOPROTEIN PREPARATIONS FOR BIOACTIVE METAL ION DELIVERY AND TEETH REMINERALISATION

(76) Inventors: Patrick Joseph Silcock, 73 Ann Street, Dunedin (NZ); Lynton Alexander Bridger, 71 Pacific Parade, Army Bay, Whangaparoa, Auckland (NZ); Adrian Stewart Denham Kerr, 100 Litten Road, Howick, Auckland (NZ); Martin Mitchell Ferguson, 342 Highgate, Dunedin (NZ); Jean-Pierre Ghislain Dufour, 6 Royal Terrace, Dunedin (NZ)

( * ) Notice: Subject to any disclaimer, the term of this patent is extended or adjusted under 35 U.S.C. 154(b) by 190 days.

(21) Appl. No.: 10/531,435

(22) PCT Filed: Oct. 20, 2003

(86) PCT No.: PCT/NZ03/00232

§ 371 (c)(1),
(2), (4) Date: Oct. 7, 2005

(87) PCT Pub. No.: WO2004/035077

PCT Pub. Date: Apr. 29, 2004

(65) Prior Publication Data
US 2006/0135407 A1 Jun. 22, 2006

(30) Foreign Application Priority Data
Oct. 18, 2002 (NZ) ...................... 522071

(51) Int. Cl.
A23J 3/10 (2006.01)
A61K 6/00 (2006.01)
A61K 47/42 (2006.01)
A61K 38/00 (2006.01)

(52) U.S. Cl. ................. 514/775; 514/773; 530/360; 530/350; 530/352; 530/332; 530/415; 530/407; 433/215; 433/228.1

(58) Field of Classification Search ............. None
See application file for complete search history.

(56) References Cited

U.S. PATENT DOCUMENTS

| 3,654,083 | A | * | 4/1972 | Cornelis et al. | ............. 435/177 |
| 4,261,819 | A | * | 4/1981 | Winter | ........................ 210/688 |
| 5,130,123 | A | * | 7/1992 | Reynolds et al. | ............... 424/49 |
| 5,223,286 | A | * | 6/1993 | Selbak | ......................... 426/94 |
| 5,981,475 | A | * | 11/1999 | Reynolds | ........................ 514/6 |

FOREIGN PATENT DOCUMENTS

WO WO 93/22930 11/1993

OTHER PUBLICATIONS

Lauber et al. (Jun. 2001) On the influence of non-enzymatic crosslinking of caseins on the gel strength of yoghurt, Nahrung/Food, vol. 45, No. 3, pp. 215-217.*

Stefanie (2008, updated) Toothpaste—Suspension or solution, Argonne, http://www.newton.dep.anl.gov/askasci/chem03/chem03984.htm, pp. 1-3.*

Vitkova et al. (2002) Optimisation of Indirect Competitive ELISAs of α-, β-, and κ-caseins for the recognition of thermal and propeolytic treatment of milk and milk products, Czech J. Food Sci., vol. 20, No. 2, pp. 53-62.*

Carbonaro et al. (2000) Composition and calcium status of acid whey from. pasteurized, UHT-treated and in-bottle sterilized milks, Nahrung, vol. 44, No. 6, pp. 422-425.*

Sparre et al. (2003) Intrauterine programming of fetal islet gene expression in rats—effects of maternal protein restriction during gestation revealed by proteome analysis, Diabetologia, vol. 46, No. 11, pp. 1497-1511.*

Wilkinson P. C. (1972) Characterization of the Chemotactic Activity of Casein for Neutrophil Leucocytes and Macrophages, Exerientia, vol. 15, pp. 1051-1052.*

Wikipedia (2008, undated) Calcium phosphate, http://en.wiikipedia.org/wiki/Calcium_phosphate, p. 1.*

Tait et al. (1997) Rapid and effective separation of strontium from liquid milk with a cation exchange resin Dowex 50WX8 treated with cryptand 222, J. Radioanaly. Nuclear Chem.,vol. 226, Nos. 1-2, pp. 225-228.*

Lacroix et al. (2006) Compared with casein or total milk protein, digestion of milk soluble proteins is too rapid to sustain the anabolic postprandial amino acid requirement, Am. J. Clin. Nutr., vol. 84, No. 5, pp. 1070-1079.*

Lundén et al. (1997) Marked effect of β-lactoglobulin polymorphism on the ratio of casein to total protein in milk, J. Dairy Sci., vol. 80, pp. 2996-3005.*

Garcia-Risco et al. (1999) Proteolysis, protein distribution and stability of UHT milk during storage at room temperature, J. Sci. Food Agricul., Vo. 79, pp. 1171-1178.*

Villa et al. (1999) Estimation of the fraction of an ingested dose of fluoride excreted through urine in pres-school children, Commun. Dent. Oral Epidemiol., vol. 27, pp. 305-312.*

Holt et al. (2003) Substructure of bovine casein micelles by small-angle X-ray and neutron scattering, Colloids Surf. A, Physicochem Eng. Aspects, vol. 213, pp. 275-284.*

(Continued)

Primary Examiner—Jon P Weber
Assistant Examiner—Samuel W Liu
(74) Attorney, Agent, or Firm—Knobbe Martens Olson & Bear LLP

(57) ABSTRACT

The invention provides, in one aspect, compositions for delivering a bioactive metal ion to a mammal, the compositions comprising (a) an effective amount of a source of the bioactive metal ion, (b) a phosphoprotein preparation obtained by partially cross linking a partial hydrolysate of casein or a caseinate, and (c) one or more physiologically acceptable diluents or carriers. Also provided are compositions for remineralising tooth enamel and/or for treating or preventing dental caries, tooth erosion, dentinal hypersensitivity or gingivitis in a mammal, wherein the compositions comprise an effective amount of such a phosphoprotein preparation, in combination with one or more carriers or diluents. In related aspects, the invention provides methods of using such compositions. Also provided are novel phosphoprotein preparations suitable for use in such compositions and methods.

17 Claims, 11 Drawing Sheets

OTHER PUBLICATIONS

Panouillé et al. (2005) Aggregation and gelation of micellar casein particles, J. Colloid. Interface Sci., vol. 287, No. 1, pp. 85-93.*

An overview of milk (2008, updated) http://animalsci.agrenv.mcgill.ca/courses/450/topics/2.html, pp. 1-7.*

Aboumahmoud et al., "Crosslinking of whey protein by transglutaminase," *J. Dairy Sci.*, 1990, pp. 256-263, vol. 73.

Aoki et al., "Caseins are cross-linked through their ester phosphate groups by colloidal calcium phosphate," *Bilchimica et Biophysica Acta*, 1987, pp. 238-243.

Aoki et al., "The least number of phosphate groups for crosslinking of casein by colloidal calcium phosphate," *J. Dairy Sci.*, 1992, pp. 971-975, vol. 75.

O'Sullivan et al., "Influence of transglutaminase treatment on some physico-chemical properties of milk," *Journal of Dairy Research*, 2002, pp. 433-442, vol. 69.

Zhang et al., "Behavior of calcium and phosphate in artificial casein micelles," *J. Dairy Sci.*, 1996, pp. 1722-1727, vol. 79.

* cited by examiner

PHOSPHOPROTEIN PREPARATIONS FOR BIOACTIVE METAL ION DELIVERY AND TEETH REMINERALISATION

REFERENCE TO RELATED APPLICATIONS

The present application is the U.S. National Phase of International PCT application number PCT/NZ2003/000232, filed Oct. 20, 2003, which claims priority to New Zealand patent application number 522071, filed Oct. 18, 2002, each of with is incorporated by reference herein.

FIELD OF THE INVENTION

This invention relates to compositions and methods for delivering bioactive metal ions to humans and animals. It also particularly relates to compositions and methods for remineralising teeth and/or for preventing or treating dental caries and/or tooth erosion, dentinal hypersensitivity or gingivitis.

BACKGROUND OF THE INVENTION

Dental caries (or decay) and dental erosion are still widespread conditions, despite the fluoridation of the water supply in many countries and the use of fluoride toothpastes. Dental caries usually begins in the enamel of the tooth surface but may progressively destroy the hard tissues of the teeth. In many countries, about half of 5 year old children experience some tooth decay. In addition, some groups of people are, by virtue of their occupation, particularly susceptible to dental erosion and/or caries. For example, wine tasters and athletes such as elite cyclists who frequently sip on sports drinks, continually expose their teeth to low pH beverages which may cause the whole surface of the tooth to dissolve.

It is well known that dairy products have a protective effect against the development of dental caries. A number of investigations have suggested that it is primarily the protein component of dairy products, and casein in particular, that exerts an anticariogenic/remineralising action on tooth enamel. In addition, a particular fraction of active peptides in casein have been identified as being largely responsible for the anticariogenic/remineralising action. These are the calcium phosphate sequestering phosphopeptides, which constitute about 10% of the total weight of casein. These peptides contain a cluster of phosphoseryl residues [-Ser(P)-Ser(P)-Ser(P)-Glu-Glu] that markedly increase the solubility of calcium phosphate by forming colloidal casein phosphopeptide amorphous calcium phosphate complexes.

There are numerous patent publications directed to various compositions containing casein, caseinates, digests thereof or specific casein-derived phosphopeptides for use in caries inhibition and related dental applications.

For example, NZ patent specification 199891 describes toothpastes and dentifrices containing a caries and gingivitis inhibiting amount of casein, alpha-s-casein or phosvitin.

JP 59152317 describes an oral composition comprising mutanase (a drug for preventing tooth decay) together with casein, casein hydrolysate or a mixture thereof.

U.S. Pat. No. 5,833,953, JP 9002928 and U.S. Pat. No. 5,427,769 all describe various compositions for treating or preventing dental caries and containing micellar casein.

U.S. Pat. No. 5,130,123 describes a dentifrice composition for inhibiting caries or gingivitis containing a water soluble salt of either a caseinate or a digest of a caseinate.

WO 82/03008 describes compositions for inhibiting caries and gingivitis, containing phosphoproteins or phosphopolypeptides containing a specified amino acid sequence, and in particular sodium caseinate, calcium caseinate or phosvitin.

JP 4077415 describes a dental calculus-preventing composition containing casein phosphopeptides in combination with a suitable excipient.

U.S. Pat. No. 5,015,628 describes anticariogenic phosphopeptides having 5 to 30 amino acids and containing a specified amino acid sequence, and which may be obtained by tryptic digestion of casein.

WO 98/40406 describes specific calcium phosphopeptide complexes having anticaries efficacy. The phosphopeptides contain the Ser(p) cluster sequence motif [-Ser(P)-Ser(P)-Ser(P)-Glu-Glu], where Ser(P) is phosphoserine, and are said to be able to stabilize their own weight in amorphous calcium phosphate and amorphous calcium fluoride phosphate.

WO 00/06108 describes various formulations for the delivery of bioactive constituents to biological surfaces such as dental surfaces, comprising suspensions or solutions of one or more isolated and purified casein protein or salt thereof.

Compositions containing casein phosphopeptides have been reported as having superior anticaries/remineralising activity compared to compositions containing intact casein. However, the use of casein phosphopeptides has the disadvantage that digestion of casein (for example using the enzyme trypsin) to release the desired phosphopeptides also releases hydrophobic peptides which give the resulting digest a bitter flavour. This means that, for the product to have an acceptable flavour, fractionation of the digest to remove such hydrophobic peptides is required. In turn, this means that only a fraction of the casein-derived material is used; typically over 75% of the material is wasted.

The applicants have now surprisingly found that by partially hydrolyzing casein and subsequently partially cross-linking the partial hydrolysate, phosphoprotein preparations having superior calcium-binding and teeth remineralisation properties to those of unmodified casein or a partial casein hydrolysate can be obtained. Such phosphoprotein preparations have also been found to have an enhanced ability to bind other bioactive active metal ions.

JP 4-126039 describes a method of preparing a functional peptide by partially hydrolyzing a food protein, such as a protein obtained from soy beans, wheat or sweetcorn, or animal proteins such as gelatin, animal meat, fish meat or casein, followed by treatment of the resultant hydrolyzed peptide with transglutaminase or diluted acid. The resulting treated peptide is said to be free of bitterness. JP 4-126039 does not however describe the cation binding properties of such peptides, nor is a peptide obtained from casein specifically described therein.

WO 00/05972 and WO 01/0154512 describe chewing gum compositions containing casein or a modified casein such as polymerized hydrolyzed casein, as part of the elastomeric component of the gum. These publications do not however describe the cation binding properties of such modified casein.

It is an object of the present invention to provide methods and/or compositions useful for delivering bioactive metal ions, and methods and/or compositions for remineralising teeth, and/or preventing or treating dental caries, tooth erosion, dentinal hypersensitivity or gingivitis, which will go some way towards overcoming the disadvantages of the prior art, or at least provide the public with a useful choice.

SUMMARY OF THE INVENTION

In a first aspect, the invention provides a composition for delivering a bioactive metal ion to a mammal, the composition comprising an effective amount of a source of the metal ion, a phosphoprotein preparation obtained by partially cross linking a partial hydrolysate of casein or a caseinate, and one or more physiologically acceptable diluents or carriers.

In another aspect, the present invention provides a method of delivering a bioactive metal ion to a mammal, comprising administering to the mammal a composition comprising an effective amount of a source of the metal ion in combination with a phosphoprotein preparation, wherein the phosphoprotein preparation has been obtained by partially cross linking a partial hydrolysate of casein or a caseinate.

In a further aspect, the invention provides the use, in the preparation of a composition for delivering a bioactive metal ion to a mammal, of a phosphoprotein preparation obtained by partially cross linking a partial hydrolysate of casein or a caseinate.

Preferably, the metal ion is divalent.

In preferred embodiments, the metal ion is selected from the group consisting of calcium, iron, zinc, cobalt, copper and magnesium.

Preferably, the composition is an oral composition, in the form of a foodstuff or beverage, or a pharmaceutical vehicle such as a tablet or capsule.

Preferably, the pH of the composition is between about 6 and 9, more preferably between about 6.5 and 8, still more preferably between about 6.8 and 7.7, and most preferably between about 7 and 7.5.

In a further aspect, the invention provides a composition for remineralising tooth enamel and/or for treating or preventing dental caries, tooth erosion, dentinal hypersensitivity or gingivitis in a mammal, wherein the composition comprises an effective amount of a phosphoprotein preparation in combination with one or more carriers or diluents, wherein the phosphoprotein preparation has been obtained by partially cross linking a partial hydrolysate of casein or a caseinate.

In still a further aspect, the present invention provides a method for remineralising tooth enamel and/or for treating or preventing dental caries, tooth erosion, dentinal hypersensitivity or gingivitis in a mammal, the method comprising contacting the teeth of the mammal with a composition comprising an effective amount of a phosphoprotein preparation, wherein the phosphoprotein preparation has been obtained by partially cross linking a partial hydrolysate of casein or a caseinate.

In still a further aspect, the invention provides the use, in the preparation of a composition for remineralising tooth enamel and/or for treating or preventing dental caries, tooth erosion, dentinal hypersensitivity or gingivitis in a mammal, of a phosphoprotein preparation obtained by partially cross linking a partial hydrolysate of casein or a caseinate.

In preferred embodiments, the composition further comprises a source of calcium ions.

Preferably, the composition also comprises a source of phosphate ions.

More preferably, the composition comprises both calcium and phosphate ions, conveniently added as calcium phosphate. Alternatively, the calcium and phosphate ions may be added as sodium phosphate and calcium chloride.

In a particular preferred embodiment, the source of calcium ions comprises natural milk calcium, such as that available under the trade name ALAMIN®.

Preferably, calcium ions are present in the composition at a level of at least about 5 mmol calcium ions per gram of phosphoprotein preparation, more preferably at least about 10 mmol/g, still more preferably at least about 20 mmol/g, more preferably at least about 30 mmol/g.

Preferably, the molar ratio of calcium ions to phosphate ions is in the range of about 0.8-1.2:0.4-0.8, more preferably about 1:0.6.

In another alternate embodiment, the composition comprises a source of strontium ions. Preferably, in this embodiment the composition also comprises a source of fluoride ions.

In certain preferred embodiments, the composition is in the form of a foodstuff such as cheese, conveniently a processed cheese, or a confection, such as a chewing gum.

In alternative preferred embodiments, the composition is in the form of a mouthwash or a dentifrice, such as a liquid dentifrice, a toothpaste, a powder, an emulsion or a gel.

Preferably the partial hydrolysate is obtained by enzymatic hydrolysis of acid casein, rennet casein or a caseinate.

Preferably, the enzyme is trypsin, conveniently bovine derived trypsin or porcine pancreatic trypsin.

Preferably, the partial hydrolysis is carried out at a pH of from about 7 to about 8.

Preferably, the degree of hydrolysis is in the range of about 3% to about 8%, more preferably about 3.5 to about 7%, such as about 4% to about 6.5%, of the total number of peptide bonds.

Preferably, the degree of hydrolysis is such that about 10% or less, more preferably about 5% or less, of the casein or caseinate is rendered insoluble at pH 7, by the partial hydrolysis.

Preferably, the partial hydrolysate is partially cross linked enzymatically, using the enzyme transglutaminase, preferably at a pH of from about 7 to about 8.

Preferably, the degree of partial cross lining is such that the resulting phosphoprotein preparation comprises about 10 μmol or more cross links per gram of protein, more preferably between about 10 and about 250 μmol/g protein, more preferably between about 50 and 160 μmol/g protein, such as between about 110 and 150 μmol/g protein.

In a further aspect, the present invention provides a novel phosphoprotein preparation, wherein the phosphoprotein preparation has been obtained by partially cross linking a partial hydrolysate of casein or a caseinate, and wherein the degree of partial hydrolysis of the casein or caseinate prior to cross linking is in the range of about 3% to about 8%, more preferably about 3.5 to about 7%, such as about 4% to about 6.5%, of the total number of peptide bonds, and the degree of partial cross linking is such that the phosphoprotein preparation comprises about 10 μmol or more cross links per gram of protein, more preferably between about 10 and about 250 μmol/g protein, more preferably between about 50 and 160 μmol/g protein, such as between about 110 and 150 μmol/g protein.

While the invention is broadly as defined above, it is not limited thereto and also includes embodiments of which the following description provides examples.

BRIEF DESCRIPTION OF THE DRAWINGS

The invention will now be described in more detail and with reference to the accompanying drawings, in which.

DESCRIPTION OF THE INVENTION

Figure 1:
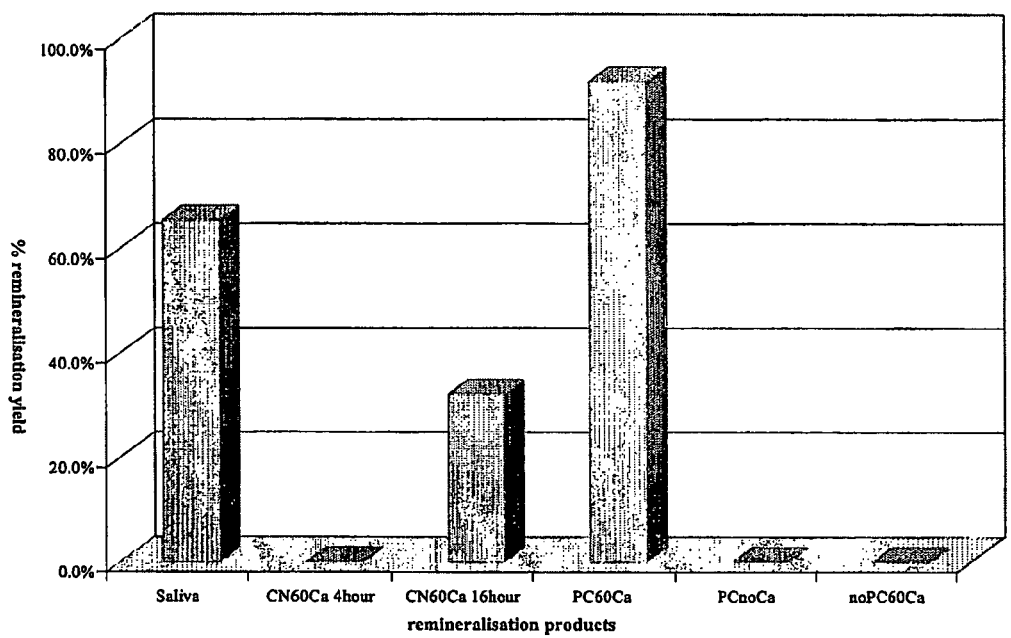
FIG. 1 shows the enamel remineralisation yield after treatment of acid etched tooth enamel with three different remineralising solutions, namely saliva, 10% caseinate solution, and 10% partially cross linked hydrolyzed caseinate solution (as described in Example 3)

As defined above, the present invention relates to methods and compositions for delivering bioactive metal ions to mammals. It also relates to methods and compositions for remineralising tooth enamel and/or for treating or preventing dental caries, tooth erosion, dentinal hypersensitivity or gingivitis. In a related aspect, the invention also relates to novel phosphoprotein preparations useful in such methods and compositions.

The applicants have surprisingly found that by partially hydrolyzing casein or a caseinate and subsequently partially cross linking the partial hydrolysate, the resulting phosphoproteins have both an increased solubility in the presence of divalent cations and an increased ability to bind divalent cations when compared to the non cross-linked partially hydrolysed casein.

These properties make such phosphoprotein preparations useful as delivery vehicles for administering bioactive metal ions to humans or animals, particularly divalent cations including calcium, iron, zinc, cobalt, copper and magnesium. The phosphoprotein preparations are able to bind significant quantities of cations and thus prevent precipitation of and maintain salts of the cations in solution, thereby enhancing their bioavailability. Also, as the phosphoprotein preparations have been found to have a higher solubility than unmodified casein, they can be incorporated into oral compositions relatively easily.

The phosphoprotein preparations have particular application in remineralising tooth enamel and thereby in treating or preventing tooth erosion or dental caries. Without wishing to be bound by any theory, it is believed that the ability of the phosphoprotein preparations to solubilise calcium (and phosphate) ions may be at least partly responsible for their ability to remineralise tooth enamel. In particular, the phosphoprotein preparations are able to maintain a high concentration of calcium and phosphate ions in solution close to the tooth enamel surface, facilitating diffusion of these ions back into the pores of demineralised tooth enamel and thus increasing remineralisation activity. The phosphoprotein preparations have also been found to form a coating on the tooth enamel surface, which may further enhance the availability of calcium and phosphate ions.

Moreover, the applicants have also surprisingly found that the phosphoprotein preparations inhibit the adhesion of caries-causing bacteria, in particular *Streptococcus mutans* to the enamel surface. As the bacteria need to adhere to the tooth surface to initiate the caries process, reducing the degree of adhesion of the bacteria can reduce the risk of caries formation. Accordingly, the phosphoprotein preparations of the present invention possess not only a reparative, remineralisation function, but also a preventative function. The applicants have also found that the protein can inhibit the adhesion of the yeast *C. albicans*, which is involved in oral thrush.

The phosphoprotein preparations suitable for use in the invention may be obtained by partially cross linking a partial hydrolysate of casein, that is, casein in which some, but not all, of the peptide bonds have been hydrolyzed.

The casein used to prepare the partial hydrolysate may be in any form; acid casein, rennet casein or a caseinate may all be used. Although chemical hydrolysis is by no means excluded, it is preferred that the partial hydrolysis is carried out enzymatically, in aqueous solution. Suitable enzymes for performing the partial hydrolysis include proteases such as trypsin and chymotrypsin. It is however particularly preferred that that the enzyme used is trypsin, conveniently bovine derived trypsin or porcine pancreatic trypsin.

The partial hydrolysis may be carried out at a temperature and pH appropriate to the enzyme being used. For example, if bovine derived trypsin is used, the partial hydrolysis may conveniently be carried out at a pH of about 7 to about 8, and at a temperature of about 37° C. It will be appreciated that at this pH, the casein will be present as a caseinate, eg sodium caseinate, depending on the buffer used in the reaction solution.

The reaction should be carried out for a sufficient period of time and under appropriate conditions, eg enzyme and casein concentrations, to allow the desired degree of hydrolysis to be achieved. When the desired degree of hydrolysis has been achieved, the reaction may conveniently be terminated, or at least substantially terminated, by inactivating the enzyme, for example by heating the reaction mixture to a temperature which will denature the enzyme, eg about 80° C. It is not critical that the hydrolysis reaction be completely terminated, provided the partial cross linking reaction as discussed below is commenced once the desired degree of hydrolysis has been achieved. That is, a minor amount of hydrolysis may still continue while the partial cross linking reaction is being carried out.

It is preferred that the partial hydrolysis is carried out under conditions which result in the partially hydrolyzed casein having a degree of hydrolysis in the range of about 3% to about 8%, more preferably about 3.5% to about 7%, such as about 4% to about 6.5%, in terms of the percentage of the original peptide bonds hydrolysed.

It is also preferred that the degree of hydrolysis is such that about 10% or less, more preferably about 5% or less, of the casein or caseinate is rendered insoluble at pH 7, by the partial hydrolysis process.

The degree of hydrolysis may be measured by methods known to those skilled in the art, conveniently by the TNBS (2, 4, 6-trinitrobenzene sulfonic acid) method.

Preferably, the molecular weight profile of the partially hydrolyzed casein or caseinate is less than that of casein but greater than the following distribution: about 1.7%≧30,000 Da, 22%<30,000 Da and ≧21,000 Da, 22%<21,000 Da and ≧12,000 Da, 54.3%<12,000 Da.

More preferably, the molecular weight profile of the partially hydrolyzed casein or caseinate is less than that of casein but greater than the following distribution: about 9.4%≧30,000 Da, 48%<30,000 Da and ≧21,000 Da, 11%<21,000 Da and ≧12,000 Da, 31.6%<12,000 Da.

More preferably, the molecular weight profile of the partially hydrolyzed casein or caseinate is less than that of casein but greater than the following distribution: about 11%≧30,000 Da, 50%<30,000 Da and ≧21,000 Da, 10%<21,000 Da and ≧12,000 Da, 29%<12,000 Da.

Most preferably, the molecular weight profile of the partially hydrolyzed casein or caseinate is less than that of casein but greater than the following distribution: about 13%≧30,000 Da, 53%<30,000 Da and ≧21,000 Da, 8%<21,000 Da and ≧12,000 Da, 26%<12,000 Da.

The molecular weight profile of the partially hydrolyzed casein may conveniently be measured by size exclusion gel filtration, using techniques known to those persons skilled in the art. By way of example, the partially hydrolyzed casein may be dissolved in a suitable solvent, conveniently 6M urea, and the protein fractions separated using fast protein liquid chromatography (FPLC system), for example using a Superdex 200 10/30HR column, and the eluted proteins detected by UV absorption (conveniently at 280 nm). The molecular weight distribution of the eluted proteins may then be calculated by integration of the protein absorption curve. Those skilled in the art will appreciate that the protein absorption curve will be dependent on the choice of buffer and buffer concentration.

Those persons skilled in the art will appreciate that by varying the reaction conditions appropriately, such as the reaction time and enzyme concentration, a partially hydrated casein having the desired degree of hydrolysis can be obtained. By way of example, a partially hydrolyzed casein having a suitable degree of hydrolysis may be obtained by first solubilizing a 10% isoelectric precipitated casein solution with NaOH to pH 7 at 50° C. The solution is then cooled to 37° C., and a porcine pancreatic trypsin preparation (a suitable preparation commercially available from Novozymes® under the product name Novo.4500K, molecular weight 23,400 Da, activity 4500 USP (United States Pharmacopaeia) units/mg) added at about 0.01% w/v casein and incubated for 15 minutes. Enzyme inactivation may be achieved by heating to 80° C. and holding for 5 minutes.

Once the partially hydrolyzed casein has been prepared, it is then partially cross linked to form a phosphoprotein preparation according to the invention.

As used herein, the term "cross linking", when used in the context of partially cross linking a partial hydrolysate of casein or a caseinate, means the formation of intermolecular covalent bonds between the amino acid residues of the casein molecules and/or casein molecule fragments comprising the partial hydrolysate. Preferably, the intermolecular covalent bonds comprise bonds between glutamine and lysine residues, ie glutamyl/lysyl covalent bonds. It will also be appreciated that some intramolecular cross linking, ie between amino acid residues on the same casein molecule or casein fragment, is likely to occur.

The term "partial", when used in the context of "partial cross linking", means that not all of the amino acid residues are cross-linked, ie that some non-cross linked amino acid residues will remain following the cross linking reaction.

The degree of partial cross linking is expressed herein in terms of micromoles of cross links per gram of protein.

The degree of partial cross linking, in terms of the quantity of glutamyl/lysl bonds, may conveniently be determined by high performance liquid chromatography (HPLC), by carrying out a proteolytic digestion of the cross-linked proteins using suitable enzymes, conveniently pronase, leucine aminopeptidase, prolidase and carboxypeptidase, followed by HPLC of the proteolytic digest and quantification of the ε-(γ-Glutamyl)lysine (G-L) peak.

The partial cross ling may conveniently be carried out enzymatically, using either of the enzymes lysyl oxidase or transglutaminase.

It is particularly preferred that the enzyme transglutaminase is used, and that the polymerization is carried out at a pH between about 7 and 8. The partial cross linking is desirably carried out under conditions and for a time sufficient to allow the desired degree of cross linking to take place. It is preferred that the reaction be carried out under conditions such that the degree of cross linking in the resulting phosphoprotein preparation comprises about 10 μmol or more cross links per gram of protein, more preferably between about 10 and about 250

μmol/g protein, more preferably between about 50 and 160 μmol/g protein, such as between about 110 and 150 μmol/g protein.

Again, once the desired degree of cross linking has been achieved, the reaction can be terminated by inactivation of the enzyme, typically by heating the reaction mixture to a temperature sufficient to denature the enzyme, for example to about 80° C. for about 5 minutes. It is also generally preferred that, following completion of the partial cross linking and deactivation of the enzyme, the resulting phosphoprotein-containing solution is dialyzed or diafiltered to remove any remaining low molecular weight peptides and salts, conveniently using a membrane with a molecular weight cutoff of from about 10,000 to about 14,000 Da. The purified phosphoprotein-containing solution may be freeze dried or spray dried to obtain the phosphoprotein preparation in a solid form.

Any commercially available source of transglutaminase can be used to carry out the partial cross linking. By way of example, a suitable enzyme is a 1% transglutaminase preparation commercially available from Ajinomoto Co. as Activa MP.

Alternatively, the plastein reaction (which is an enzymatic reaction known to those skilled in the art) may be used. The cross linking may also be carried out between tyrosine residues using peroxidase and hydrogen peroxide.

Although it is preferred that partial cross linking of the partial casein hydrolysate is carried out enzymatically, partial cross linking by chemical means, using a suitable reagent such as a bifunctional aldehyde (eg glutaraldehyde) is not excluded.

Those persons skilled in the art will appreciate that by varying the reaction conditions appropriately, such as the reaction time and enzyme concentration, a phosphoprotein preparation having the desired degree of cross linking can be obtained.

By way of example, a phosphoprotein preparation having a suitable degree of cross linking may be obtained by treating a partially hydrolyzed casein prepared as described above with a transglutaminase preparation (Activa MP, commercially available from Ajinomoto Co.) added at a ratio of 4.5% w/w casein and incubating the reaction mixture at 40° C. for 18 hours.

The phosphoprotein preparations may be incorporated into compositions suitable for delivering bioactive metal ions, particularly divalent metal ions, to humans and animals. Such compositions may be in the form of pharmaceutical vehicles such as tablets or capsules. Tablets or capsules containing the phosphoprotein preparation, in combination with a source of a bioactive metal ion in a physiologically useful amount and one or more physiologically acceptable carriers or diluents, may be prepared using standard methods known to those skilled in the art. The desired quantities, ie effective amounts, of the source of bioactive metal ion to be incorporated in the compositions of the present invention will vary depending on the particular cation in question and the amount in which it is required by the mammal for whom the composition is intended, for example whether it is a trace mineral such as iron, zinc, manganese, molybdenum, copper, chromium, or is required in larger amounts, such as calcium.

Alternatively, the phosphoprotein preparation may be incorporated into a foodstuff or beverage, in combination with a source of the bioactive metal ion it is desired to administer. For example, compositions containing the phosphoprotein preparations in combination with an effective amount of a source of calcium (such as calcium phosphate) or iron may be administered to humans or animals in need of calcium or iron supplementation, respectively.

The phosphoprotein preparations also have particular application in remineralising teeth, and in treating or preventing tooth erosion, dental caries, dentinal hypersensitivity or gingivitis.

Compositions useful in such applications and suitable for contacting teeth with the phosphoprotein preparation may take a number of forms. For example, such compositions may take the form of a mouthwash or a dentifrice, such as a liquid dentifrice, toothpaste, a powder, an emulsion or a gel containing the phosphoprotein. Alternatively, the phosphoprotein preparations may be incorporated into foodstuffs, such as cheese, for example processed cheese, or confectionery such as chewing gum.

It is preferred that, in addition to the phosphoprotein preparation, such compositions also contain a source of calcium ions, and preferably also a source of phosphate ions. For example, calcium phosphate may be included in the composition. Although calcium and phosphate ions are present in saliva, incorporating sources of these ions is preferred in order to take advantage of the calcium-binding properties of the phosphoprotein and maximize the concentration of calcium and phosphate ions in contact with the tooth enamel.

It is particularly preferred that calcium ions are present in the composition at a level of at least about 5 mmol calcium ions per gram of phosphoprotein preparation, such as at least about 10 mmol/g, such as about 20 mmol/g, such as about 30 mmol/g. It is also preferred that the molar ratio of calcium ions to phosphate ions is in the range of about 0.8-1.2:0.4-0.8, more preferably about 1:0.6.

In some particularly preferred embodiments, the source of calcium ions comprises natural milk calcium phosphate, in which the calcium is generally in the form of calcium hydroxyapatite.

Natural milk calcium phosphate is commercially available, with a particularly preferred embodiment being that available from New Zealand Milk Products Ltd under the trade name ALAMIN®, which comprises calcium, phosphate, and also protein, lactose, fat, moisture, sodium, potassium and chloride, in the following typical proportions:

| | |
|---|---|
| Total mineral content 70% (w/w): | 28% calcium and 48% phosphate |
| Protein (N × 6.38) | 7% |
| Lactose | 4% |
| Fat | 1% |
| Free moisture | 3% |
| Bound moisture | 8% |
| Calcium | 28,000 mg/100 g |
| Phosphorus | 16,000 mg/100 g |
| Sodium | 400 mg/100 g |
| Potassium | 300 mg/100 g |
| Chloride | 100 mg/100 g |

Natural milk calcium phosphate may be obtained by methods known in the art, typically by clarifying and pasteurizing acid whey permeate, cooling and ultrafiltering the permeate, followed by heating, pH adjustment and holding at the elevated temperature such that the minerals including calcium phosphate will be precipitated, and recovery of the precipitate.

Another suitable source of natural milk calcium phosphate is the product available under the trade mark Lactoval® from DMV International.

Other anions that may be included in the compositions include fluoride and fluorophosphate.

In other embodiments, the compositions may include a source of strontium ions in addition to or instead of calcium ions. Such compositions may be particularly useful in treating dentinal hypersensitivity.

It is generally preferred that the pH of the compositions of the present invention, either in the form of compositions for delivering bioactive metal ions or for dental applications as described above, is buffered at a level between about 6 and 9, more preferably between about 6.5 and 8, still more preferably between about 6.8 and 7.7, and most preferably between about 7 and 7.5.

In one embodiment of the invention, a processed cheese product is provided, which includes a phosphoprotein preparation as described above, in combination with natural milk calcium phosphate. In this embodiment of the invention, it will be appreciated that the product acts both as a source of dietary calcium as well as having remineralising/anticaries properties.

The processed cheese component of the product is preferably present in an amount of about 90 to about 98% by weight of the product, such as about 94 to about 96% by weight, typically about 95% by weight The phosphoprotein preparation may typically comprise about 0.5 to about 3% by weight of the product, such as about 1 to about 2%, typically about 1.2 to about 1.6% by weight. The natural milk calcium phosphate may typically comprise about 0.5% to about 4.5% by weight of the product, such as about 2 to about 3.5%, typically about 2.5% to about 3% by weight.

In another specific embodiment of the invention, a composition in the form of an emulsion is provided, comprising a phosphoprotein preparation as described herein in combination with natural milk calcium, conveniently that commercially available as ALAMIN®. The phosphoprotein preparation may conveniently be present in an amount of about 1% to about 15% by weight of the emulsion, such as about 5% to about 12%, typically about 9% to 11%. The natural milk calcium phosphate may be present in an amount of about 3% to about 12% by weight of the emulsion, such as about 5% to about 10%, typically about 6 to about 9% by weight. The emulsion will preferably include one or more additional components, such as emulsifiers, thickeners, flavourings and sweeteners. Such additional components may be chosen from those known in the art as suitable for use in emulsion type formulations for dental use.

The invention will now be described in more detail with reference to the following non-limiting examples.

EXAMPLES

Example 1

Phosphoprotein Preparation and Calcium Binding

Tryptic Hydrolysis

A 10% isoelectric precipitated casein solution was solubilised with NaOH to pH 7.0 at 50° C. Once soluble, the solution was cooled to 37° C., and bovine derived trypsin (Novo) added at between 0.01-0.2% w/w casein, incubated for up to 2 hours, then heated to 80° C. and held for 5 minutes.

| Lot number MAP10 | Enzyme concentration % weight/weight casein | Hydrolysis time/ minutes | Degree of Hydrolysis |
|---|---|---|---|
| Lot 5 | 0.01 | 15 | 5.7 |
| Lot 6 | 0.01 | 30 | 6.0 |
| Lot 7 | 0.01 | 45 | 6.3 |
| Lot 1 | 0.01 | 60 | 7.0 |

The molecular weight profiles of the phosphoprotein preparations were determined by gel filtration as follows. A 1% protein solution was prepared in 6M Urea, with 50 mM sodium phosphate at pH 7.5 as the buffer. This solution was centrifuged at 10 000×g for 10 minutes and passed through a 0.2 μm filter. A sample volume of 500 μl injected into the 100 μl sample loop of a Pharmacia FPLC fitted with a Superdex 200 10/30HR column. The running buffer was 6 M Urea, with 50 mM sodium phosphate at pH 7.5 and flow rate of 0.5 ml/mm. Detection was by UV absorption (280 nm). The protein absorption curve was integrated and arbitrarily divided into the following four molecular weight groupings:
1) greater than about 30,000 Daltons
2) less than about 30,000 Daltons and greater than about 21,000 Daltons
3) less than about 21,000 Daltons and greater than about 12,000 Daltons
4) less than about 12,000 Daltons.

Molecular Weight Profiles of Lots 5, 6, 7 and 1 (After Partial Hydrolysis), Expressed as % Distribution of Lots 5, 6, and 1

| | Lot number | | | |
|---|---|---|---|---|
| Molecular weight range | 5 | 6 | 7 | 1 |
| ≧30,000 | 13.66 | 11.66 | 9.4 | 9.84 |
| <30,000, ≧21,000 | 53.74 | 50.78 | 49.13 | 48.87 |
| <21,000, ≧12,000 | 7.58 | 9.99 | 11.37 | 10.92 |
| <12,000 | 25.02 | 27.57 | 30.1 | 30.37 |

Transglutaminase Treatment

The pH was re-adjusted (as necessary) to 7.0, and transglutaminase (1% commercial preparation, Ajinomoto) added at a ratio of 4.5% w/w casein and incubated at 40° C. for the desired length of time. Enzyme inactivation was achieved by heating to 80° C., and holding for 5 min. The modified protein solutions were freeze dried.

Number of Cross Links Formed After Treatment with Transglutaminase, Expressed as μmol Crosslinking Protein for Lots 5, 6, 7 and 1

| | Cross-linking time (hours) | | |
|---|---|---|---|
| Lot number | 1 | 6 | 18 |
| Lot 5 | 50 | 98 | 168 |
| Lot 6 | 51 | 90 | 152 |
| Lot 7 | 55 | 95 | 150 |
| Lot 1 | 57 | 109 | 159 |

Measurement of Calcium Binding Capacity of the Phosphoprotein Preparations

The calcium binding capacity of the proteins was determined by re-suspending the protein in water, adding calcium and phosphate ions at a set ratio under constant pH; removing the insoluble material (salts and protein); then removing the soluble non bound salts and determining the amount of calcium bound to the soluble protein. The experimental details were as follows.

A 1% solution of the proteins were dissolved with milli-Q water, and allowed to stand for 1 hour to ensure complete hydration. Calcium chloride was added at the following levels: 0 mM, 10 mM, 20 mM, 30 mM, 40 mM and 50 mM; and the solution incubated at 25° C. for 1 hour with good mixing. Sodium phosphate was added at a molar ratio of 0.6 to the calcium. Throughout the experiment the pH was maintained at 7.0 using NaOH solution. The samples were incubated at 25° C. for 6 to 10 hours with good mixing. After incubation, a sample was centrifuged at 10 000×g for 10 minutes and filtered through a 0.2 μm nylon filter and split into two portions.

One portion of the sample was injected into a 2 ml sample loop and loaded onto a Pharmacia FPLC fitted with Sephadex G-25 (Vt=25 ml) desalting column. The running buffer was 10 mM HEPES at pH 7 the flow rate was 2 ml/min and detection was achieved through UV absorption (280 ηm), conductivity and pH. The protein peak was collected and calcium concentration determined by atomic absorption spectroscopy (AAS).

The other portion was used to determine the soluble protein content as per the Folin protein assay.

Calcium Binding Capacity of Lot 5 Before (0 Hours) and After Transglutaminase Treatment (1, 6, or 18 Hours) Expressed as mg $Ca^{2+}$ per g Initial Protein

| mmol $Ca^{2+}$ added | Hours treated with transglutaminase | | | |
|---|---|---|---|---|
| | 0 | 1 | 6 | 18 |
| 30 | 3.2 | 7.3 | 24.2 | 31.2 |
| 40 | 1.1 | 1.2 | 34.7 | 37.6 |

Calcium Binding Capacity of Lot 6 Before (0 Hours) and After Transglutaminase Treatment (1, 6, or 18 Hours) Expressed as mg $Ca^{2+}$ per g Initial Protein

| mmol $Ca^{2+}$ added | Hours treated with transglutaminase | | | |
|---|---|---|---|---|
| | 0 | 1 | 6 | 18 |
| 30 | 9.3 | 32.3 | 32.1 | 40.2 |
| 40 | 0.0 | 2.6 | 7.1 | 4.2 |

Calcium Binding Capacity of Lot 7 Before (0 Hours) and After Transglutaminase Treatment (1, 6, or 18 Hours) Expressed as mg $Ca^{2+}$ per g Initial Protein

| mmol $Ca^{2+}$ added | Hours treated with transglutaminase | | | |
|---|---|---|---|---|
| | 0 | 1 | 6 | 18 |
| 30 | 16.1 | 24.6 | 28.5 | 32.0 |
| 40 | 3.0 | 2.4 | n/a | 7.4 |

Calcium Binding Capacity of Lot 1 Before (0 Hours) and After Transglutaminase Treatment (1, 6, or 18 Hours) Expressed as mg $Ca^{2+}$ per g Initial Protein

| mmol $Ca^{2+}$ added | Hours treated with transglutaminase | | | |
|---|---|---|---|---|
| | 0 | 1 | 6 | 18 |
| 30 | 24.6 | 16.0 | 21.9 | 36.4 |
| 40 | 2.4 | 1.9 | 6.1 | 21.1 |

Calcium Binding Capacity of Caseinate Expressed as mg $Ca^{2+}$ per g Initial Protein

| mmol $Ca^{2+}$ added | mg $Ca^{2+}$ bound |
|---|---|
| 0 | 0.0 |
| 5 | 2.8 |
| 10 | 2.3 |
| 15 | 1.7 |

The different proteins described above represent a range of degrees of hydrolysis of casein (Lot 5 the least hydrolysed, Lot 1 the most), and a range of cross-linking of the hydrolysis products with transglutaminase (0 hours, no cross-linking and 18 hours the most cross linked). Lot 5 proteins are the most resistant to $Ca^{2+}$ induced precipitation with near maximum calcium loading 40 mg Ca/g protein still remaining soluble in a 40 mM $Ca^{2+}$ solution.

With a greater degree of hydrolysis of the casein, the proteins, even after extensive Tg cross-linking, become less resistant to precipitation in the presence of higher $Ca^{2+}$ concentrations. None of the non-cross linked samples were resistant to precipitation, and resistance increased with greater cross-linking in all samples.

The ability of native casein to bind $Ca^{2+}$ is demonstrated in the final table. It is rapidly precipitated with increasing $Ca^{2+}$ concentrations and has a maximum binding of just 2.8 mg $Ca^{2+}$/g casein at 5 mM $Ca^{2+}$.

The caseinate results illustrate the surprising nature of the partially cross-linked hydrolysed casein solubility/binding results that proteins with an average molecular weight similar to unmodified caseinate (or greater than caseinate) should bind substantially more calcium ions and remain soluble.

Example 2

Preparation of a Phosphoprotein

Tryptic Hydrolysis

A 10% isoelectric precipitated casein solution was solubilised with NaOH to pH 7.0 at 50° C. Once soluble, the solution was cooled to 37° C., and porcine derived trypsin (Novo.4500K, molecular weight 23,400 Da, activity 4500 USP units/mg) added at 0.01% w/w casein and incubated for 15 minutes. Enzyme inactivation was achieved by heating to 80° C., and holding for 5 minutes.

Molecular Weight Profiles of Lot 5

| Molecular weight range | |
|---|---|
| ≧30,000 | 13.66 |
| <30,000, ≧21,000 | 53.74 |
| <21,000, ≧12,000 | 7.58 |
| <12,000 | 25.02 |

Transglutaminase Treatment

The pH was re-adjusted (as necessary) to 7.0, and transglutaminase (1% commercial preparation, Activa MP, Ajinomoto Co) added at a ratio of 4.5% w/w casein and incubated at 40° C. for 18 hours. Enzyme inactivation was achieved by heating to 80° C., and holding for 5 min. The molecular weight material greater than 30,000 Da was increased by 100%.

Example 3

Teeth Remineralisation (Hardening)

The remineralising (rehardening) potential of three products was determined. The products were human saliva, caseinate solution and a phosphoprotein preparation obtained by partial cross linking of partially hydrolyzed casein. The remineralising efficacy of the products was determined by measuring the recovery in hardness of the controlled acid etched human enamel following treatment.

Enamel Preparation

The human unerupted third molars were used in all of the experiments. After extraction, the teeth were mechanically cleaned with anylac brush and deionised water, and stored until required in 10% buffered formalin solution (pH 7.0) at 4° C.

Before use, the teeth were thoroughly rinsed, cut longitudinally and then were embedded in epoxy resin (Araldite). Each specimen was hand-ground on a glass plate using silicon carbide grits, progressively of 240- to 600-grit, under running water. Fine polishing was achieved using the 8-inch Laps with 3-μm diamond abrasive for 5 minutes and with 1-μm diamond abrasive for another 5 minutes on a rotating polishing machine using distilled water to keep specimens moist. Between each polishing treatment, an ultrasonic bath was used for removing debris. The specimens were evaluated under a dissecting microscope (15x) and those with any evidence of cracks, flaws, developmental defects or extraction damage were rejected. The selected samples were stored until required in 10% buffered formalin solution (pH 7.0) at 4° C.

Enamel Demineralisation

The polished sound enamel specimens were individually demineralised in 25 ml of 1% (w/v) citric acid solution for 10 minutes at 37° C. to create eroded lesions. Following demineralisation, specimens were washed thoroughly with deionised water and stored in deionised water prior to the next step. The pH of the solution was 2.3.

Remineralisation

Preparation of the Remineralisation Products

Saliva: Submandibular saliva was collected from a healthy volunteer and 10 mmol/L sodium azide added. Twenty-five milliliters of saliva was used for each specimen in the remineralising procedure.

10% Caseinate Solution (CN-60Ca): CN-60Ca contained 36 mmol/L $(PO_4)^{3-}$ (at pH 9.0), 60 mmol/L $Ca^{2+}$ and 10% (w/v) lactic acid casein. The solution was thoroughly mixed using a magnetic stirrer at room temperature. After incubation in a water bath at 50° C. for 15 minutes and cooling to room temperature, 10 mmol/L sodium azide was added as a preservative and then adjusted to pH 7.5 with 10% (w/v) NaOH.

10% Phosphoprotein Solution (PC-60Ca): PC-60Ca consisted of 36 mmol/L $(PO_4)^{3-}$ (at pH 9.0), 60 mmol/L $Ca^{2+}$ and 10% (w/v) phosphoprotein preparation obtained by partial cross linking of partially hydrolyzed caseinate (PC). The phosphoprotein preparation was obtained by treating a caseinate solution having a degree of hydrolysis of approximately 4% with the enzyme transglutaminase, as described in Example 2. Other conditions were as described for CN-60Ca7.5.

Protocol for Enamel Remineralisation

The selected specimens were treated in separate remineralisation solutions. The specimens were immersed in 40 ml of fresh remineralisation solution (under constant shaking) for four hour time periods at 37° C. in individual sealed 80-ml beakers. The CN60Ca was also incubated for a 16 hour time period.

Evaluation of Demineralisation/Remineralisation

Surface Microhardness (SMH) Evaluation

The surface microhardness (SMH) of the enamel blocks were measured with a Leitz MiniLoad-Hardness instrument using a Vickers diamond under a 200 g load for 20 seconds. The specimens were held perpendicular to the indentor to the compound stage of the hardness instrument. Fifteen indentations were averaged on each surface of the individual specimens for surface hardness determinations (after standardisation of the diamond indenter and using the 400× magnification). A distance of at least two times the indentation lengths for enamel was kept between the indentations to minimise interactions between neighbouring indentations. The SMH readings were taken at three stages of enamel demineralisation/remineralisation model as follows: (1) before exposure to the demineralisation solution (DS), (2) after exposure to the DS (1% citric acid) and softening and (3) after exposure to remineralisation solution or control solution. Following the initial examination of SMH (stage 1), each specimen underwent 10 minutes of demineralisation at 37° C. in DS. Each specimen was immersed individually in 25 ml of solution. After exposure, the specimens were then removed from the solution, washed thoroughly in deionised water, blotted dry with 3 mm filter paper and taken for SMH re-examination (stage 2). After the selected remineralisation treatment, the specimens were removed from the solution, thoroughly washed in deionised water, blotted dry again and re-tested for SMH (stage 3). The softening and rehardening potentials of the DS and the different remineralisation solutions were calculated for each specimen by subtracting the baseline SMH value (stage 1) and rehardening value (stage 3), respectively, from the softening value (stages 2).

The relationship between the measured SMH and the length of the Vickers indent average of the two diagonals was determined by equation 1:

$$SMH(kg/mm2)=1854\times P/d2 \quad [1]$$

where P is the load in grams and d is the average length of the diagonals of the indentation measured in microns. The SMH numbers are directly from the microscopic measurements with Leitz MiniLoad-Hardness instrument used in the present study. In order to compare quantitatively the SMH numbers for the de- and remineralised specimens on a linear scale, it was necessary to convert the pre- and post-SMH measurements to values proportional to the yield of change between softened SMH and the amount of remineralisation achieved. For comparison between these two results, the difference of the remineralising effect was calculated using equation 2:

$$R(\%)=[(PSMH)3-(PSMH)2]/[100-(PSMH)2]\times 100\% \quad [2]$$

where PSMH3 and PSMH2 mean as follows:

$PSMH3 = [SMH$ of stage $3/SMH$ of stage $1]\times 100\%$ $PSMH2 = [SMH$ of stage $2/SMH$ of stage $1]\times 100\%$ Therefore R in equation 2 is the rehardening yield, remineralisation yield, or recovery yield, of stage 3 in this study.

Results

TABLE 1

Effect of submandibular saliva, caseinate solution and phosphoprotein preparation (obtained by partial cross linking of partially hydrolysed casein) on the etched enamel surface

| | Surface Microhardness (kg/mm$^2$) | | |
|---|---|---|---|
| Specimen No | Stage 1 Mean (SD) | Stage 2* Mean (SD) | Stage 3 Mean (SD) |
| Saliva for 4 hours: | | | |
| Saliva 1 | 398.6 (21.8) | 331.4 (34.3) | 380.3 (30.5) ** |
| Saliva 2 | 370.3 (13.6) | 285.0 (35.3) | 349.7 (22.3) ** |
| Saliva 3 | 405.0 (27.7) | 290.3 (26.4) | 352.6 (20.8) ** |
| Saliva 4 | 379.6 (14.9) | 293.2 (25.6) | 344.3 (17.8) ** |
| CN-60Ca for 4 hours: | | | |
| CN 4 | 350.6 (30.4) | 281.9 (15.4) | 279.1 (20.3) *** |
| CN 5 | 405.9 (29.5) | 319.7 (20.3) | 314.0 (23.2) *** |
| CN 6 | 370.4 (19.1) | 282.3 (26.7) | 293.0 (26.6) *** |
| CN 7 | 397.2 (18.6) | 313.4 (19.5) | 316.0 (15.8) *** |
| CN-60Ca for 16 hours: | | | |
| CN 8 | 394.5 (19.0) | 293.4 (33.3) | 339.1 (26.4) ** |
| CN 9 | 422.5 (24.5) | 339.8 (23.7) | 325.1 (20.1) *** |
| CN 10 | 376.5 (30.4) | 324.2 (30.7) | 362.4 (30.5) (p = 0.003) |
| CN 11 | 387.0 (20.4) | 315.8 (30.0) | 335.6 (20.5) (p = 0.015) |
| PC-60Ca for 4 hours | | | |
| PC-60Ca 1 | 356.9 (20.5) | 307.0 (23.2) | 338.5 (36.9) ** |
| PC-60Ca 2 | 411.7 (19.5) | 296.9 (22.5) | 336.7 (35.4) ** |
| PC-60Ca 3 | 378.0 (20.4) | 300.4 (15.1) | 384.9 (16.1) ** |
| PC-60Ca 4 | 374.9 (14.7) | 281.2 (19.5) | 394.9 (25.0) ** |
| PC-60Ca 5 | 379.6 (13.9) | 286.6 (19.5) | 400.3 (28.9) ** |
| PC-60Ca 6 | 365.2 (11.8) | 293.5 (26.3) | 364.3 (18.3) ** |
| PC-60Ca 7 | 374.9 (30.3) | 324.4 (30.5) | 364.9 (30.6) ** |
| PC-60Ca 8 | 405.1 (21.3) | 336.7 (19.8) | 406.5 (37.1) ** |
| PC-60Ca 9 | 388.1 (21.9) | 280.0 (36.2) | 396.7 (22.8) ** |
| PC-60Ca 10 | 399.5 (26.3) | 289.8 (09.1) | 369.3 (17.0) ** |
| Control groups: | | | |
| PC-noCa 1 | 347.6 (19.2) | 269.4 (13.7) | 277.4 (20.5) *** |
| PC-noCa 2 | 367.7 (18.7) | 302.4 (20.6) | 307.5 (25.7) *** |
| noPC-60Ca 1 | 362.5 (18.9) | 299.4 (20.6) | 278.7 (18.7) *** |
| noPC-Ca 2 | 373.0 (21.0) | 294.1 (22.2) | 291.0 (31.4) *** |

N = 15 (each specimen).
Stage 1: Microhardness testing in initial stage.
Stage 2: Microhardness testing after 1.0% citric acid etching for 10 minutes.
Stage 3: Treatment group: Microhardness testing after treatment with remineralising solution.
*All stage 2 values were significantly less than stage 1 values (P < 0.001).
** Stage 3 values were significantly greater than stage 2 values in treatment group (P < 0.001).
*** Stage 3 values were not significantly greater than stage 2 values in control group.

The Effect of Saliva on Etched Enamel Surface

Table 1 shows that human submandibular saliva significantly increased the SMH numbers of etched enamel after the four-hour treatment. The relative SMH after acid etching (Stage 2) was decreased to 77.3% of its original value and after treatment with the saliva this increased to 91.9% (Stage 3). The mean of the remineralisation yield (R) was 65.5%.

The Effect of 10% Caseinate (CN) on Etched Enamel Surface

It required 16 hours treatment with 10% caseinate solution (CN-60Ca7.5) before significant rehardening was found; there were no effects observed in the 4 hour groups. After treatment for 16 hours, SMH numbers significantly increased in three out of the four specimens (P=0.001, P<0.003, P=0.015, respectively) (Table 1). The relative SMH after acid etching (Stage 2) was decreased to 80.6% of its original value and after treatment with the caseinate solution for 16 hours this increased to 86.5% (Stage 3). The mean R was 32.1%.

The Effect of Phosphoprotein Obtained by Partial Cross Linking of Partially Hydrolyzed Casein (PC) on Etched Enamel Surface Table 1 shows the change of SMH numbers of enamel surface after treatment with the phosphoprotein preparation obtained by partial cross linking of partially hydrolyzed casein (PC) with 36 mmol/L $(PO_4)^{3-}$; 60 mmol/L $Ca^{2+}$ (PC-60Ca). The SMH numbers of etched-enamel were significantly increased after the 4 hours incubation in PC-60Ca with all ten specimens. Seven out of ten specimens almost returned to the initial (before-etching) SMH values. The SMH numbers were significantly higher than that of initial level in two tests (20%) (P=0.012) after treatment with PC-60Ca.

The relative SMH after acid etching (Stage 2) was decreased to 78.3% of its original value and after treatment with the PC solution for four hours this increased to 98.2% (Stage 3). The remineralisation yield (R) was 92.1% (n=10).

The exposure of acid etched enamel to the phosphoprotein solution without $Ca^{2+}$ (PC-noCa) or to calcium phosphate buffer with no phosphoprotein preparation (no PC-60Ca) resulted in no significant regain in hardness (Table 1).

Summary of the Performance of the Different Remineralisation Solutions on the Recovery Yield of the Etched Enamel Surface The enamel remineralisation yield is presented in FIG. 1. The difference in remineralisation yield between solutions was clear. PC-60Ca produced distinctly greater remineralisation potential than that of others.

De- and Remineralisation Assessment by Scanning Electron Microscopy (SEM)

Figure 2:
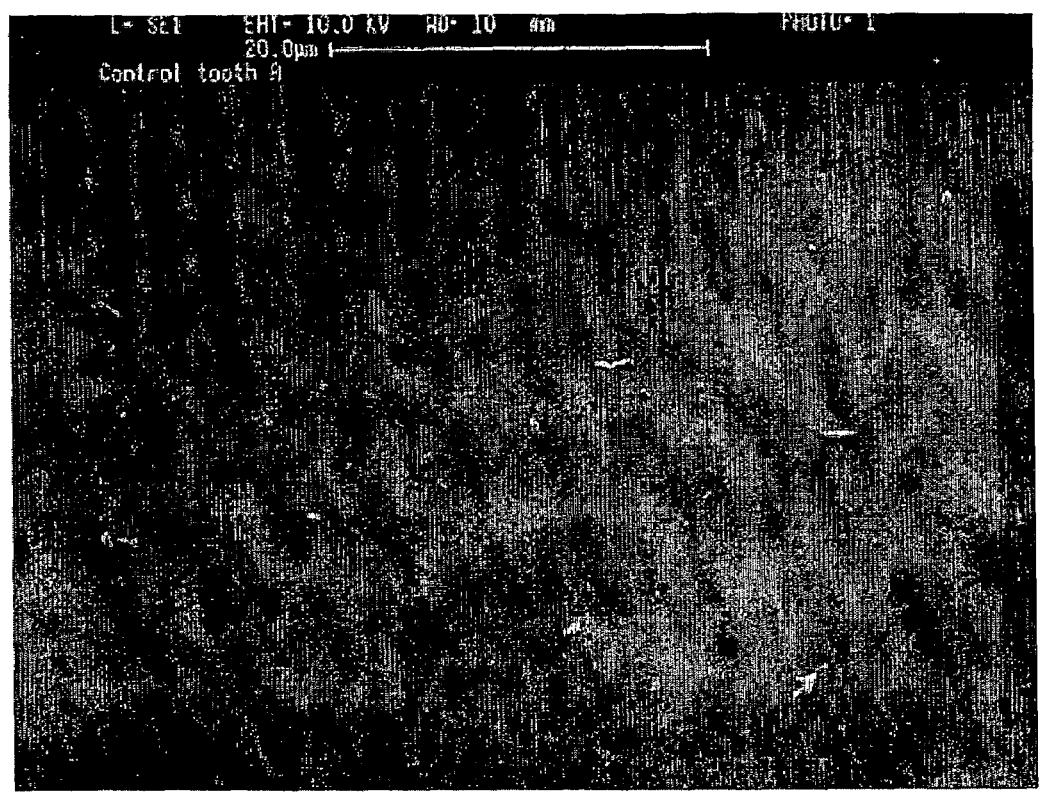
FIG. 2 is a Scanning Electron Micrograph of the tooth enamel surface prior to acid etching.
Figure 3:
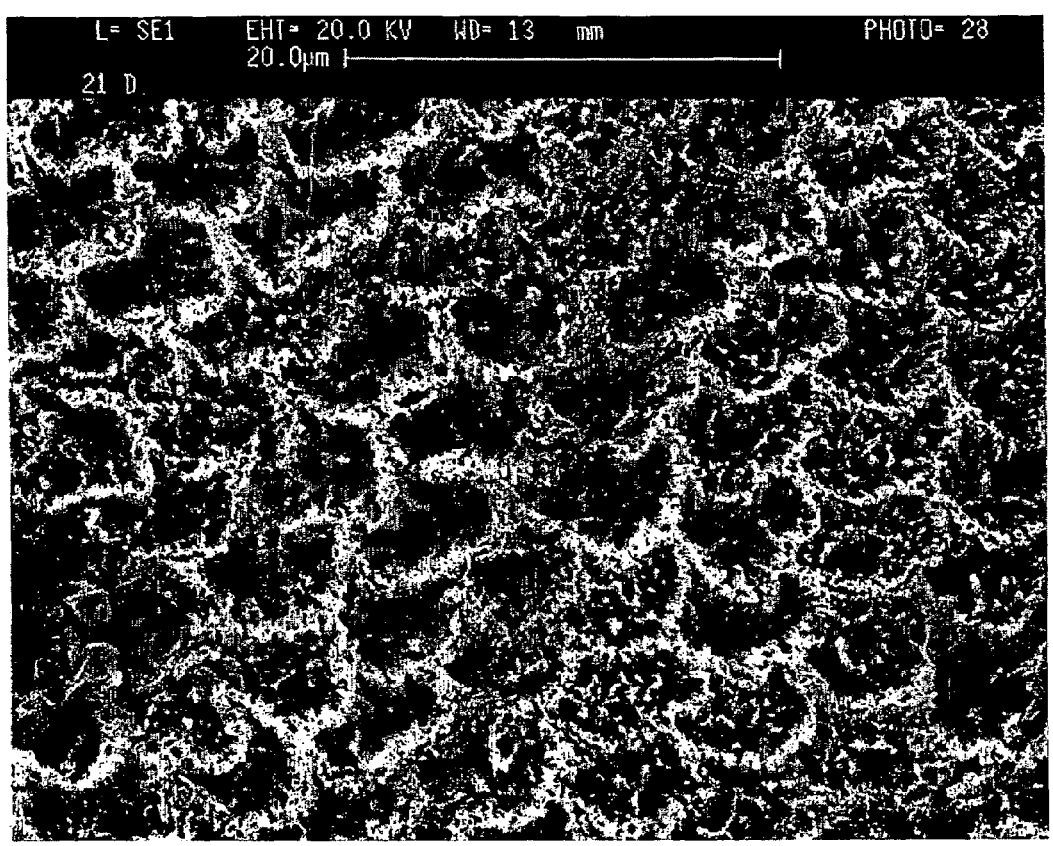
FIG. 3 is a Scanning Electron Micrograph of the tooth enamel surface after acid etching.

Examination of the enamel surface by Scanning Electron Microscopy prior to etching showed the surface to be smooth (FIG. 2). In contrast, it was found that acid etching of sound enamel resulted in (1) a loss of surface enamel, (2) an increase in the tooth surface area due to the roughening of the tooth surface and (3) exposure of a more reactive surface following the removal of superficial inert enamel (FIG. 3).

Figure 4:
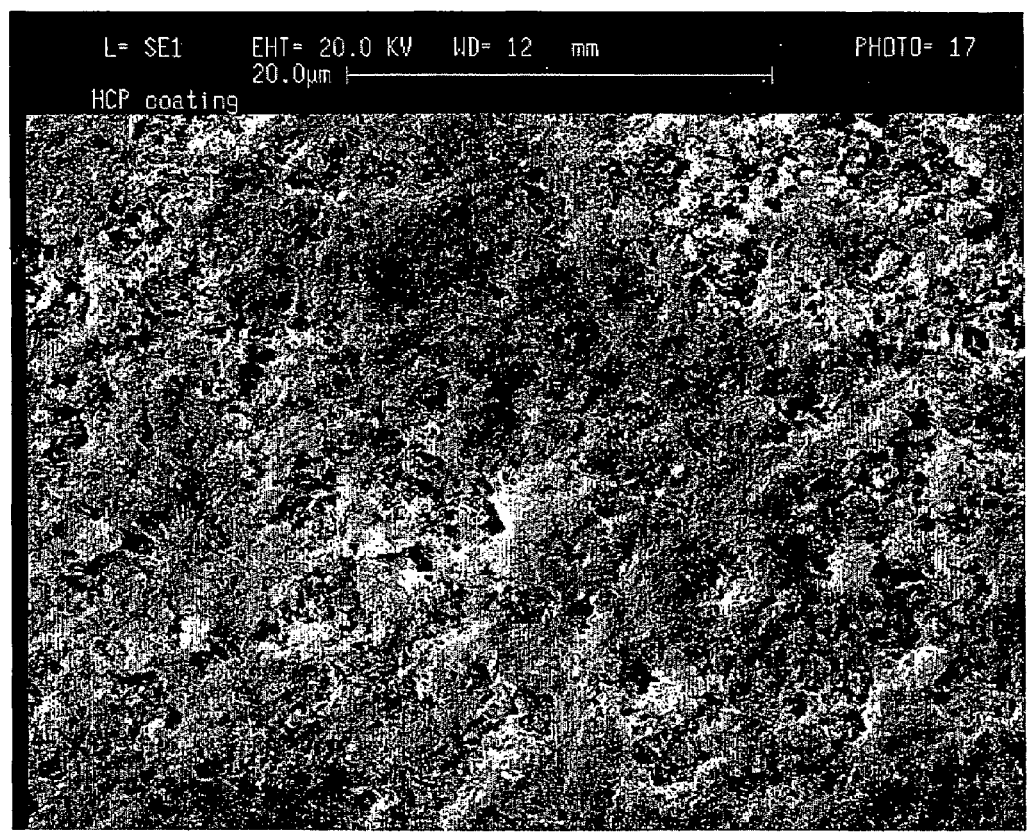
FIG. 4 is a Scanning Electron Micrograph of the tooth enamel surface after both acid etching and treatment with polymerized hydrolyzed caseinate solution.
Figure 5:
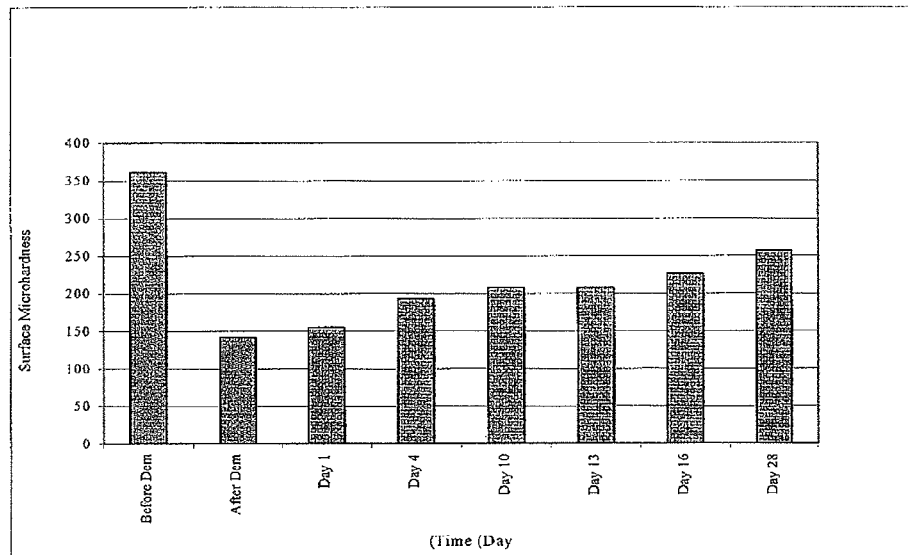
FIG. 5 shows the changes in microhardness of enamel after a demineralization treatment in 0.1 mol/L acetic acid pH 4.5 for 24 hours followed by remineralisation in a "MAP 112" phosphoprotein solution, prepared by the method of Example 4, containing 60 mmol/L calcium ions and 36 mmol/L phosphate ions.
Figure 6:
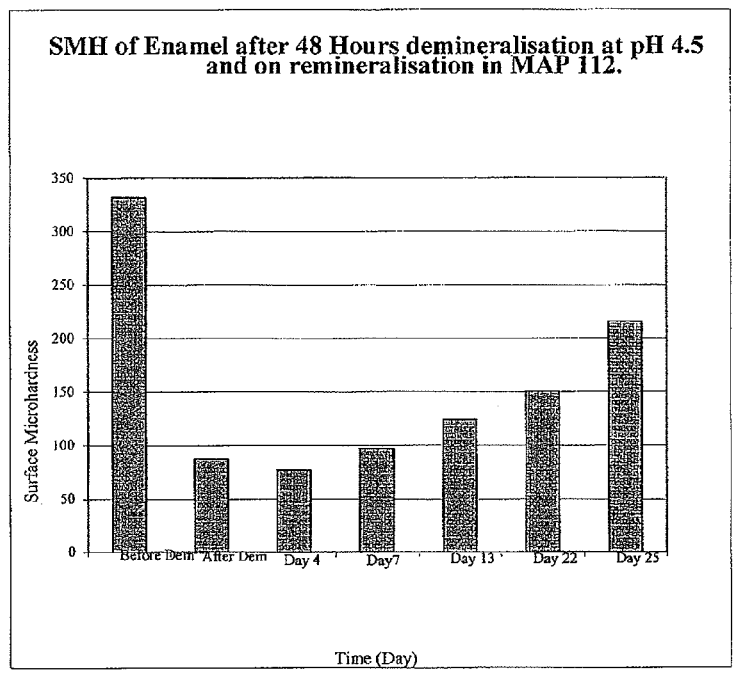
FIG. 6 shows the changes in microhardness of enamel after a demineralization treatment in 0.1 mol/L acetic acid pH 4.5 for 48 hours followed by remineralisation in a MAP 112 phosphoprotein solution containing 60 mmol/L calcium ions and 36 mmol/L phosphate ions.
Figure 7:
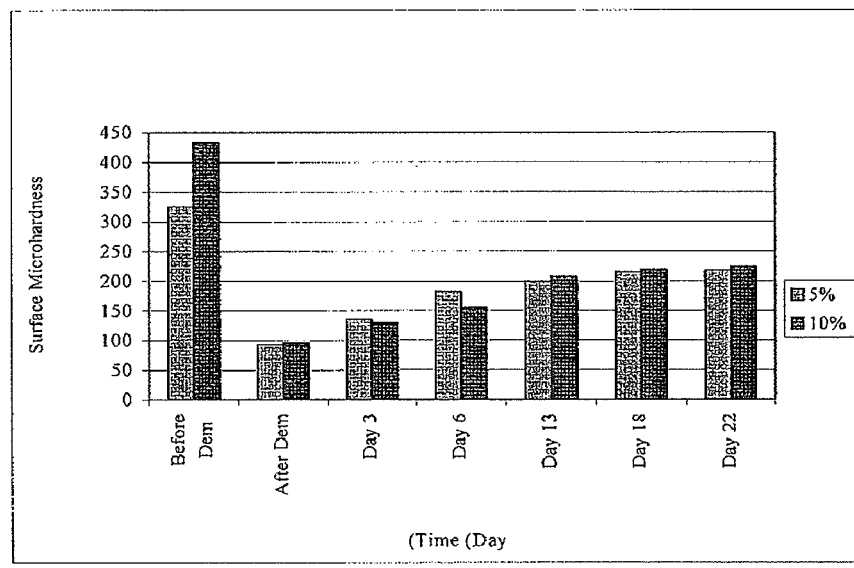
FIG. 7 shows the changes in microhardness of enamel after a demineralization treatment in 0.1 mol/L acetic acid pH 4.5 for 72 hours followed by remineralisation in a MAP 112 phosphoprotein solution containing 60 mmol/L calcium ions and 36 mmol/L phosphate ions.
Figure 8:
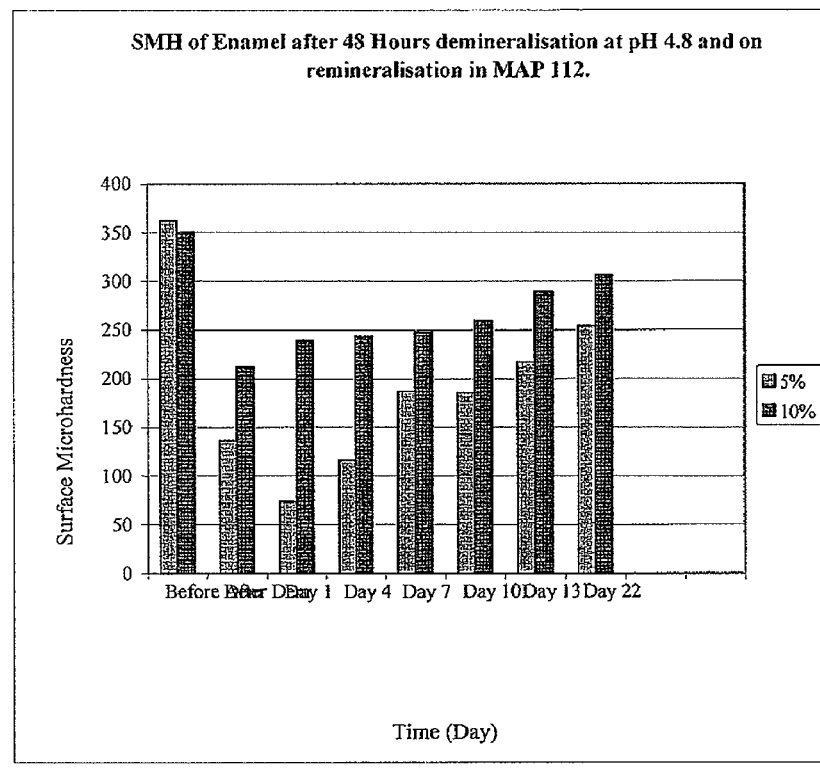
FIG. 8 shows the changes in microhardness of enamel after a demineralization treatment in 0.1 mol/L acetic acid pH 4.8 for 48 hours followed by remineralisation in a MAP 112 phosphoprotein solution containing 60 mmol/L calcium ions and 36 mmol/L phosphate ions.
Figure 9:
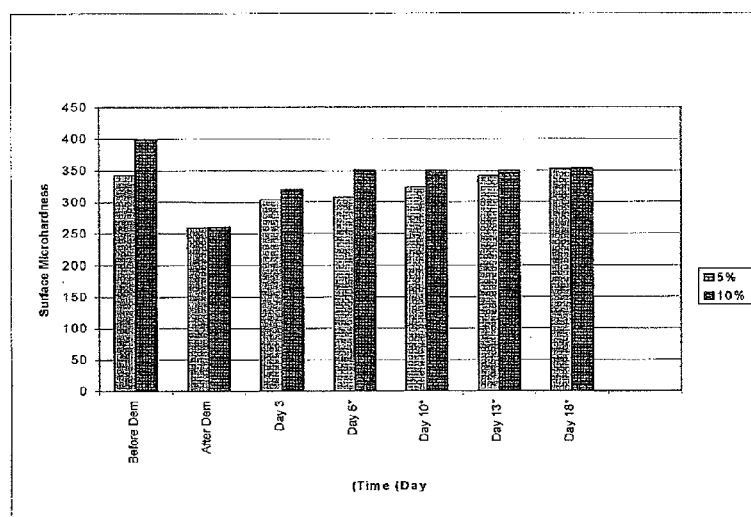
FIG. 9 shows the changes in microhardness of enamel after a demineralization treatment in 0.1 mol/L acetic acid pH 4.5 for 24 hours followed by remineralisation in a MAP 112 phosphoprotein solution containing 60 mmol/L calcium ions and 36 mmol/L phosphate ions.
Figure 10:
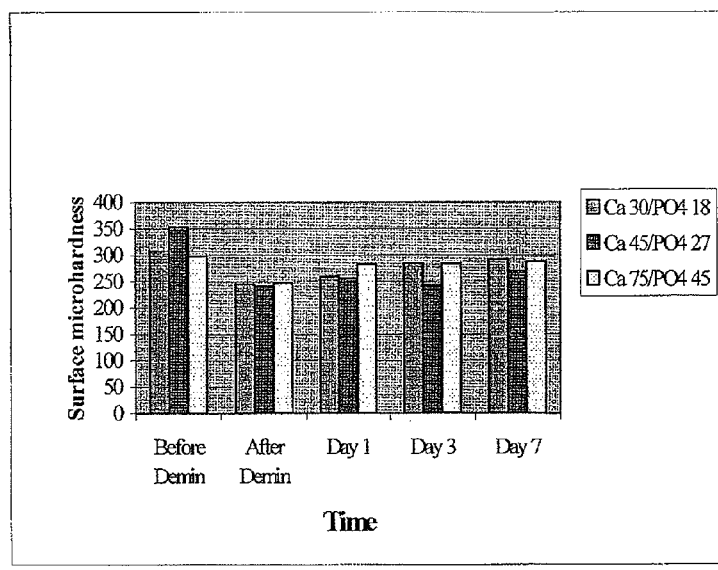
FIG. 10 shows the changes in microhardness of enamel after a caries-like demineralisation treatment followed by remineralisation in a MAP 112 solution containing 500 mg/mL hydroxyapatite and varying levels calcium and phosphate added as soluble salts.
Figure 11:
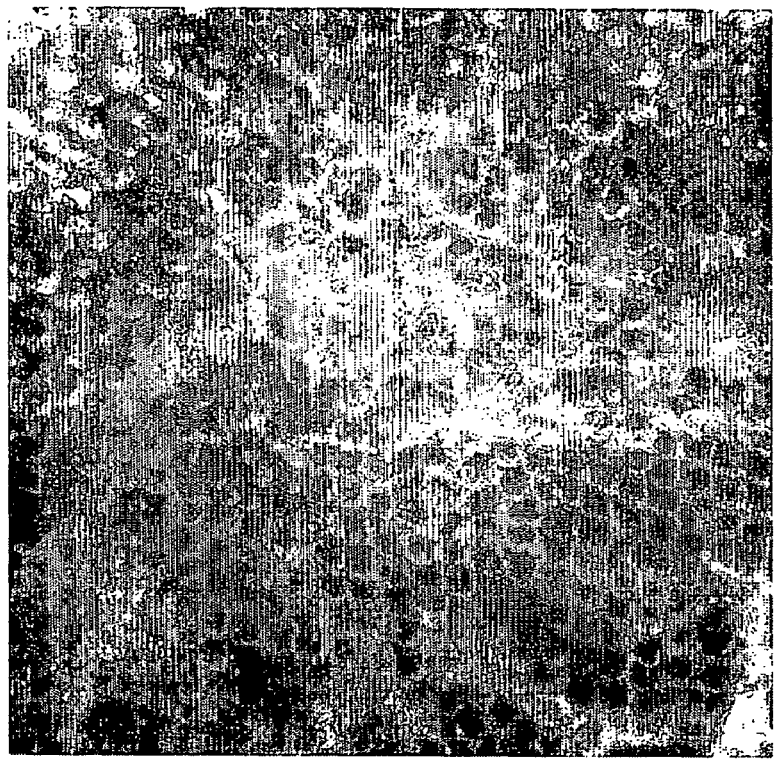
FIG. 11 is an image of a demineralised tooth enamel taken using a Zeiss Upright Confocal Microscope. Enamel was demineralised for 96 hours in a pH 4.8 buffer.
Figure 12:
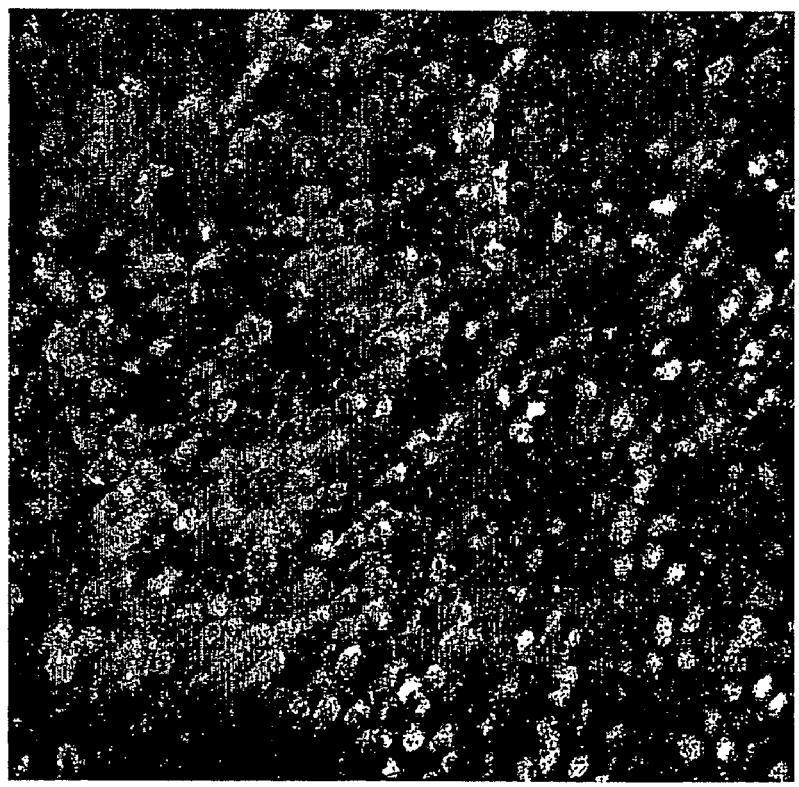
FIG. 12 is an image of a Zeiss Confocal Microscope image of demineralised tooth enamel that was remineralised in MAP112 protein containing 75 mM calcium chloride and 45 mM sodium phosphate buffer. The exposed hexagonal microstructure has been remineralised extensively leaving calcium deposits on the enamel surface.

After treatment with PC-60Ca, the etched enamel surface was covered with a relative smooth and dense coating with frequent rod-shaped products. In most areas, a moderately uniform surface coating was present with adherent reaction products of 0.5-1 μm in length The coating was sufficiently dense to obscure the enamel prisms. The distribution of the deposits was relatively homogeneous and the deposits covered almost all the enamel surface (FIG. 4). The presence of small rod-shaped products was assumed to be phosphoprotein-calcium phosphate complexes (PCCPC), though morphologic appearance alone does not identify a chemical compound. It can be seen that many rod-shaped products were present in the demineralised interprismatic regions.

Discussion

Exposure of demineralised enamel surface to remineralisation solutions showed a regain in microhardness. This may indicate a partial restoration of the calcium phosphate content. The net result was a filling up of intra- and interprismatic spaces, which was assessed directly by SEM morphological observation and indirectly by indentation length measurements. A reduced porosity of the enamel surface in the SEM causes an increased resistance to the indenter penetration into the test surface, which is reflected by a smaller indentation length and suggests that remineralisation has occurred.

Remineralisation Effect of Saliva on Etched Enamel Surface

That saliva resulted in the rehardening of the etched enamel was expected as the remineralising ability of saliva is well reported (Koulourides et al. 1965, Leach et al. 1989, Peretz et al., 1990). Saliva can be described as "the bloodstream of the teeth"—being rich in minerals and proteins and supersaturated with respect to calcium and phosphate ions. It surrounds and bathes the tooth and provides a constant supply of ions to the enamel surface (Peretz et al., 1990). When cleaned enamel is wet by saliva, specific proteins (such as statherins and proline-rich proteins) from the saliva are adsorbed onto the teeth surface to form the salivary pellicle or acquired pellicle. These two protein groups are thought to inhibit primary (spontaneous) and/or secondary precipitation (crystal growth) of calcium and phosphate from saliva. This appears to be a necessary and important activity in the oral cavity because human saliva is supersaturated with respect to most calcium phosphate salts. These precipitation inhibitors keep the saliva in a state of supersaturation. The pellicle plays an important role in protecting the enamel by serving as a diffusion barrier.

An etching or carious lesion occurs in particular locations on the enamel surface where the equilibrium is upset and where a net loss of mineral has occurred. The physical nature of the surface enamel, the saliva and the acquired pellicle can be considered as analogous to defense mechanisms present in other systems in the body.

Remineralisation Effect of Phosphoproteins Obtained by Partial Cross Linking of Partially Hydrolysed Casein (PC) and Caseinate on Etched Enamel Surface Under the experimental conditions, PC and caseinate were shown to coat on, incorporate in and reharden the etched enamel surface when assessed by microhardness testing and SEM. The SMH numbers of etched enamel showed almost complete recovery after treatment with the PC solution. The SEM showed a dense coating layer was precipitated on the enamel surface that resisted removal, even after 10 minutes of water washing. However, the crystalline nature of the surface enamel cannot be determined by the SEM method used in the present study.

The caseinate was not as effective as the PC and required a treatment time of 16 hours to achieve significant rehardening. The major reason for this was believed to be the low solubility of the caseinate in the presence of calcium and phosphate ions.

For successful rehardening of the enamel when using the PC calcium and phosphate ions had to be present. The omission of any one of the three components (phosphoprotein, calcium and phosphate) resulted in no remineralisation phenomenon being observed. Although the time period and chemical conditions (the conditions will be more complex in oral environment) are empirical, the key conclusion is that the de- and remineralisation occurred in this model system.

The possible reasons for the high remineralising ability of the phosphoprotein in conjunction with the calcium and phosphate ions are as follows:

1) The hydrolysis process followed by the partial cross linking process results in a protein with greater stability than that of caseinate. The hydrolysis treatment followed by the partial cross linking treatment appears to interfere with the self-associating nature of casein and appears to inhibit its micelle-forming tendency. Due to this decreased tendency to self associate the protein will remain soluble in the presence of high levels of calcium and phosphate.
2) The calcium phosphate rich phosphoprotein is the main component of the PC solution. The promotion of enamel remineralisation by the PC is consistent with the protein solubilising calcium and phosphate ions being at least partially responsible for remineralisation activity of casein. It is thought that the PC increased the solubility of calcium ions in solution, resulting in a higher concentration of free calcium ions available into the pores of etched enamel surface to facilitate remineralisation activity.
3) Without wishing to be bound by any theory, the remineralisation model of the phosphoprotein obtained by partial cross linking of partially hydrolysed casein may be related to its ability to coat on and incorporate in the etched enamel surface. The PC contains closely situated groups of phosphoseryl residues that bind calcium phosphate and hydroxyapatite very strongly. These sections of the protein could calcium-bridge, ionically interact, and hydrogen-bind with the enamel surface. On binding to the hydroxyapatite surface, the protein coating may act as a reservoir, releasing calcium ions available for use in remineralisation or redeposition into areas of demineralisation in the crystal lattice. As shown in the present study, casein phosphoprotein-calcium phosphate particles are present on the enamel surface of the calcium-releasing bonding systems, forming a potential protective deposit on the enamel surface. Dissolution of calcium ions from casein phosphoprotein-calcium phosphate complexes (CPPCPC) and diffusion into the pores in the enamel may have occurred.

Example 4

Preparation of a Phosphoprotein (MAP 112)

Tryptic Hydrolysis

Fifty-five kilograms of sodium caseinate was dispersed in 50° C. deionised water so that a final concentration of 522 L was achieved. The solution was cooled to 37° C., the pH adjusted to 7.06 with NaOH and porcine derived trypsin (Novo.4500K, molecular weight 23,400 Da, activity 4500 USP units/mg) added at 0.01% w/w casein and incubated for five minutes. The solution was heated to 80° C. over 15 minutes, held for four minutes and cooled to 45° C.

Molecular Weight Profile After Hydrolysis

| Molecular weight range | Percentage |
| --- | --- |
| ≧30,000 | 10.7 |
| <30,000, ≧21,000 | 57.8 |
| <21,000, ≧12,000 | 15.7 |
| <12,000 | 15.8 |

Transglutaminase Treatment

The pH was re-adjusted to 7.0, and transglutaminase (1% commercial preparation, Activa MP, Ajinomoto Co) added at a ratio of 4.5% w/w casein and incubated for 15 hours (temperature at the end of incubation was 32° C.). The solution was heated to 80° C. and held for 5 minutes. The solution was diluted to 1000 L and cooled to 5° C. The solution was ultrafiltered until a final concentration of 20% solids was achieved and then spray dried. The molecular weight material greater than 30,000 Da was increased by 100% and the number of cross-links in the protein was 92 μmol/g.

Example 5

Remineralisation of Enamel Following a Gentle Erosion Model

A second acid erosion model that provided less aggressive erosion was examined using an acetic acid-based system.

Methods

The enamel was prepared as per Example 3.

Preparation of Demineralisation Solution 24 and 48 Hours Demineralisation Solutions Two demineralisation solutions were prepared at pH 4.5 and pH 4.8 with 0.1 mol/L acetic acid and the pH adjusted with NaOH. Hydroxyapatite (HA) 750 mg/L and 500 mg/L of were added to the demineralisation solutions at pH 4.5 and pH 4.8, respectively. Sodium azide (0.05 g/L) was added to each solution as a preservative and the bottle wrapped with foil and stored at 4° C. until required.

72 Hours Demineralisation Solutions

Sample preparation procedure as above sample, except that 750 mg/L and 1.0 g/L of HA were added to the demineralisation solutions at pH 4.5 and pH 4.8, respectively.

Preparation of Remineralisation Solution

Twenty-five grams of MAP 112 protein (prepared as described in Example 4) was dispersed in 300 mL of distilled water. A 2M calcium chloride solution was added dropwise and then after 30 minutes the sodium phosphate ($Na_2HPO_4$) was added so that a final concentration of 60 mmol $Ca^{2+}$ and 36 mmol $PO_4^{3-}$ were achieved. The pH was adjusted to 7.0 using 4M NaOH and made up to volume (500 ml). Sodium azide (0.05 g/L) was added to each solution as a preservative and the bottle wrapped with foil and stored at 4° C. until required.

Protocol for Enamel Demineralisation

The specimens were demineralised in 25 ml of demineralisation solution (under constant shaking, in dark) for periods 24 hours, 48 hours and 72 hours at 25° C.

Protocol for Enamel Remineralisation

The demineralised enamel blocks were remineralised in MAP 112 protein solutions containing 60 mmol/L Ca ions and 36 mmol/L phosphate ions. The enamel blocks were immersed in 25 ml of remineralisation solution (under constant shaking) for various time periods at 25° C. in the dark. The remineralisation solution was changed every three days.

Assessment of Changes in the Enamel

Microhardness

The microhardness was measured as per Example 3 on the untreated enamel, enamel after demineralisation and at periods during remineralisation.

Results

On demineralisation all samples showed a decrease in surface microhardness (SMH) with the pH 4.5 solution showing a bigger decrease than the pH 4.8 solution. Surface changes were confirmed by light microscopy. When the remineralisation portions of the graphs are examined it can be seen that all samples show a slow increase in SMH. As discussed in Example 3 mineral content of enamel shows a strong positive relationship with SMH.

Example 6

Remineralisation of Enamel Treated to Induce Caries-like Defects

Methods

The enamel was prepared as per Example 3.

Preparation of Demineralisation Solution

The demineralising solution was prepared following the method of White D J: Use of synthetic polymer gels for artificial carious lesion preparation. *Caries Res* 21(3):228-242, 1987.

A polyacrylic acid/lactate solution, containing 0.2% polyacrylic acid (Carbopol C907) and 0.1 mol/L lactic acid was prepared as follows. Polyacrylic acid (1 g) was dissolved in 350 ml of distilled water at room temperature, 4.29 ml of lactic acid solution (87.5%) was added after polyacrylic acid had dispersed, the pH was adjusted to 4.80 (4M NaOH) and made up the volume (500 ml) and transferred the solution to 500-ml Schott bottle. Sodium azide (0.05 g/L) was added to each solution as a preservative and the bottle wrapped with foil and stored at 4° C. until required.

A saturated hydroxyapatite, polyacrylic acid/lactate solution, containing 0.2% polyacrylic acid (carbopol C907) and 0.1 mol/L lactic acid was prepared as follows. Polyacrylic acid (1 g) was dissolved in 350 ml of distilled water at room temperature, 4.29 ml of lactic acid solution (87.5%) was added after polyacrylic acid had dispersed, followed by 3.7 g of hydroxyapatite, the pH was adjusted to 4.80 (4M NaOH) and made up the volume (500 ml) and transferred the solution to 500-ml Schott bottle. Sodium azide (0.05 g/L) was added to each solution as a preservative and the bottle wrapped with foil and stored at 4° C. until required.

The final demineralisation solutions were prepared immediately prior to demineralisation by diluting the saturated hydroxyapatite Carbopol/lactate solution with the Carbopol/lactate solution with no hydroxyapatite.

About 55 ml of saturated hydroxyapatite Carbopol/lactate solution was centrifuged at 2500 rpm for 20 minutes, the 50 mL of supernatant was collected and mixed with 50 mL of the Carbopol/lactate solution with no hydroxyapatite. The pH was adjusted to 4.8.

Preparation of Remineralisation Solution at Three Different Calcium Levels

Three lots of 25 g of MAP 112 protein were dispersed in 300 mL of distilled water. A 2M calcium chloride solution was added dropwise and then after 30 minutes the sodium phosphate ($Na_2HPO_4$) was added according to following table:

| | | | |
|---|---|---|---|
| $Ca^{2+}$ (mM) | 30 | 45 | 75 |
| Weight (g) (as $CaCl_2$) | 7.50 | 11.25 | 18.75 |
| $PO_4^{3-}$ (mM) | 18 | 27 | 45 |
| Weight (ml) (as $Na_2HPO_4$) | 1.278 | 1.916 | 3.194 |

Hydroxyapatite (500 mg/L) was added to each solution, the pH was adjusted to 7.0 using 4M NaOH and made up to volume (500 ml). Sodium azide (0.05 g/L) was added to each solution as a preservative and the bottle wrapped with foil and stored at 4° C. until required.

Protocol for Enamel Demineralisation

The specimens were demineralised in 25 ml of demineralisation solution (under constant shaking, in dark) at 25° C. for 96 hours.

Protocol for Enamel Remineralisation

The enamel blocks were remineralised in MAP 112 protein solutions containing 30, 45, 60 or 75 mmol Ca ions. The enamel blocks were immersed in 25 ml of remineralisation solution (under constant shaking) for various time periods at 25° C. in the dark.

Assessment of Changes in the Enamel

Microhardness

The microhardness was measured as per Example 3 on the untreated enamel, enamel after demineralisation and at periods during remineralisation.

Example 7

*Streptococcus mutans* Adhesion Assay

Method

*Streptococcus mutans* NCTC 10449 was grown in trypone/yeast extract medium containing brain/heart infusion and radiolabelled with [$^3$H]thymidine. Hydroxyapatite beads (20 mg, Biorad) were hydrated in KCl buffer (Cannon et al., 1995) and then incubated with pooled human saliva (30% v/v KCl buffer). The beads were washed with KCL buffer and then the saliva-coated hydroxyapatite beads were incubated with radiolabelled *S. mutans* cells. Non-adherent *S. mutans* cells were removed from the beads by washing with KCl buffer and then the percentage of the cells added to each assay that adhered to the SHA beads were calculated.

MAP 111 Phosphoprotein (DH 5.0, 140 μmol cross-links/g protein) was added at the following concentrations: 0.001%, 0.01%, 0.1%, 1.0% and 10.0% (in KCl buffer). The effect of the phosphoprotein on adhesion, relative to assays containing no phosphoprotein was calculated.

Each assay was conducted in triplicate and each experiment was conducted three times.

Figure 14:
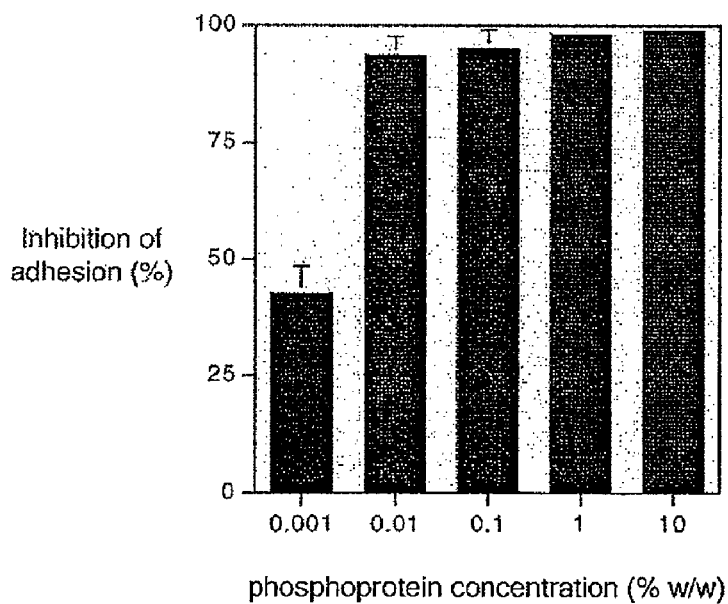
FIG. 14 shows the effect of MAP phosphoprotein concentration on the percent of *S. mutans* inhibited from adhering to hydroxyapatite beads over three experiments. It can be seen that as the concentration increases the % inhibition of adhesion increases.
Figure 15:
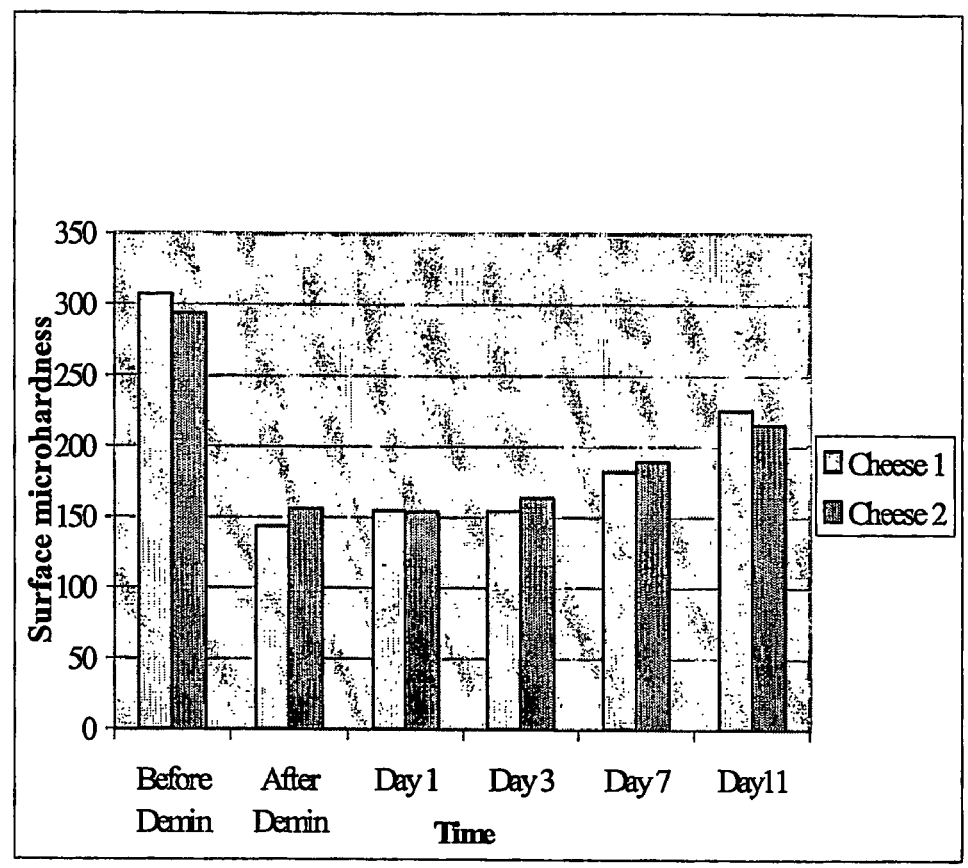
FIG. 15 shows the changes in microhardness of enamel after a caries-like demineralization treatment followed by remineralisation in a processed cheese (containing phosphoprotein MAP 112 and milk calcium phosphate) extract solution.
Figure 16:
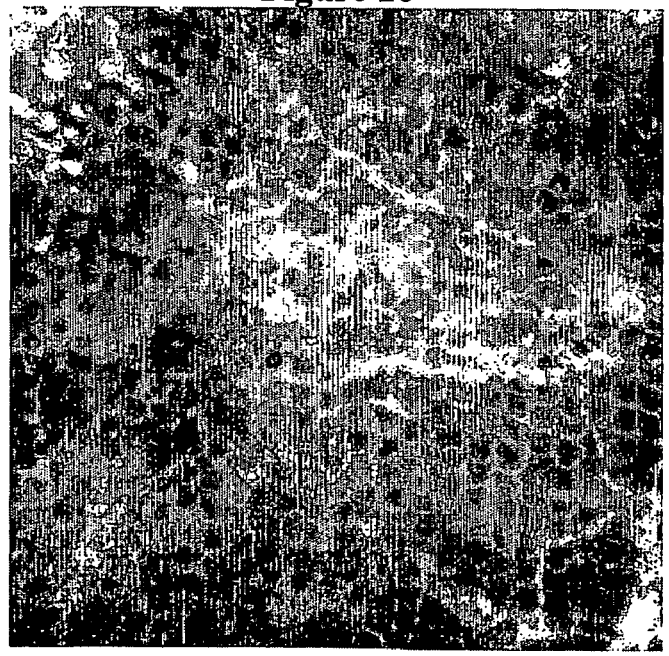
FIG. 16 is an image of a demineralised tooth enamel taken using a Zeiss Upright Confocal Microscope. Enamel was demineralised for 96 hours in pH 4.8 buffer.
Figure 17:
FIG. 17 is an image of a Zeiss Confocal Microscope image of demineralised tooth enamel that was remineralised in cheese extract. The enamel has been remineralised extensively filling in the areas between the hexagonal microstructure.

It can be seen from FIG. 14 that the protein effectively inhibited adhesion of *S. mutans* at concentrations as low 0.01% and still achieved about 40% inhibition of adhesion at 0.001% protein. For the caries process to be initiated *S. mutans* needs to adhere to the tooth surface. Hence by reducing the number of *S. mutans* adhering the risk of caries formation can be reduced. These assay results illustrate that the proteins not only possess a reparative function but also a preventative function.

Reference: Cannon, R. D., Nand, A. K. and Jenkinson, H. F. (1995) Adherence of *Candida albicans* to human salivary components adsorbed to hydroxyapatite. Microbiology 141: 213-219

Example 8

Measurement of Iron Binding Capacity of the Phosphoprotein Preparations

The iron binding capacity of the proteins was determined by re-suspending the protein in water, adding $FeCl_2$ under constant pH; removing the insoluble material (salts and protein); then removing the soluble non bound salts and determining the amount of calcium bound to the soluble protein. The experimental details were as follows.

A 1% solution of the proteins were dissolved with milli-Q water, and allowed to stand for 1 hour to ensure complete hydration. Ferrous chloride was added at the following levels: 0 mM, 10 mM, 30 mM, and 40 mM; and the solution incubated at 25° C. for 1 hour with good mixing. Throughout the experiment the pH was maintained at 7.0 using NaOH solution. The samples were incubated at 25° C. for 6 to 10 hours with good mixing. After incubation, a sample was centrifuged at 10 000×g for 10 minutes and filtered through a 0.2 μm nylon filter.

The sample was injected into a 2 ml sample loop and loaded onto a Pharmacia FPLC fitted with Sephadex G-25 (Vt=25 ml) desalting column. The running buffer was 10 mM HEPES at pH 7 the flow rate was 2 ml/min and detection was achieved through UV absorption (280 ηm), conductivity and pH. The protein peak was collected and iron concentration determined by atomic absorption spectroscopy (AAS).

Iron Binding Capacity of Lot 6 After Cross-linking with Tg for 18 Hours. Expressed as mg $Fe^{2+}$/g Initial Protein, and mg $Fe^{2+}$/g of Soluble Protein.

| [$Fe^{2+}$] | mg $Fe^{2+}$/g protein (total) | mg $Fe^{2+}$/g protein (soluble) |
|---|---|---|
| 0 mM | 0.0 | 0.0 |
| 10 mM | 2.9 | 6.4 |
| 30 mM | 3.5 | 13.8 |
| 40 mM | 3.7 | 19.5 |

$Fe^{2+}$ was found to bind to the Lot 6, 18 hr Tg phosphoprotein preparation at a maximum of 3.7 mg $Fe^{2+}$/g protein. Of the protein that remained soluble, the $Fe^{2+}$ bound at about 20 mg $Fe^{2+}$/g soluble protein.

Zinc, Iron II and Magnesium Binding Capacity of Phosphoproteins

| mmol ions added | Zinc ions | Iron II | Magnesium ions |
|---|---|---|---|
| 5 | 22.2 | 21.7 | 4.6 |
| 10 | 41.0 | 44.8 | 5.4 |
| 15 | 43.0 | 44.0 | 5.4 |

Example 9

Phosphoprotein Fortified Processed Cheese

The following two processed cheeses were prepared:

| Formulation | % weight/weight | |
|---|---|---|
| | 1 | 2 |
| Processed cheese | 95.60 | 95.42 |
| MAP (phosphoprotein) | 1.34 | 1.34 |
| Natural milk calcium phosphate | 2.87 | 2.86 |
| Calcium chloride | 0.00 | 0.19 |
| Water | 0.19 | 0.19 |

The cheeses were prepared in a Brabender W50 mixer at 45° C. and 50 RPM. The processed cheese (1 $cm^3$ cubes) was fed into the mixer over about 60 seconds, the water added and mixed for three minutes. The preblended natural milk calcium phosphate and MAP 112 were added and mixed for ten minutes. The mixer was stopped, the cheese mixture was removed, formed into a block, wrapped in cling film and stored at 5° C. until required.

Remineralisation Potential of Modified Processed Cheese.

The enamel was prepared as per Example 3, the demineralisation was conducted as per Example 6 and the remineralisation was as per Example 6 except that a cheese slurry preparation was used in place of the remineralising solution. The microhardness was measured as per Example 3.

Cheese Slurry Preparation

The modified processed cheeses contained about 20% protein almost all of which was casein. Fifty-five grams of modified processed cheese was weighed and blended (with Waring Blender, high speed) with 144 ml of distilled water for 5 minutes at room temperature. The cheese slurry was centrifuged for 20 minutes at 4,350 g and the aqueous solution (middle layer) and the fatty supernatant were carefully transferred to a separating flask. The mixture was left to separate and the aqueous phase removed. Sodium azide (0.05 g/L) was added to each solution as a preservative and the bottle wrapped with foil and stored at 4° C. until required.

Results

Microhardness

The demineralisation achieved a good reduction in surface hardness and as mentioned earlier this is strongly correlated with enamel mineral concentrations. On remineralisation a slow increase in SMH can be seen. This increase in SMH suggests the enamel is being remineralised.

Example 10

Remineralising Emulsion Formulation

| Ingredients | % weight/weight |
|---|---|
| Phosphoprotein MAP112 | 10.00 |
| Natural Milk Calcium Phosphate (Alamin) | 7.50 |
| Sorbitol | 4.50 |
| GMS 400V | 1.00 |
| Propyl paraben | 0.075 |
| Methyl paraben | 0.025 |
| Medium chain triglycerides | 7.50 |
| Glycerol | 1.00 |
| Delios S | 30.00 |
| Xanthan gum solution (0.1%) | 38.30 |
| Peppermint Oil | 0.074 |

Method

The dry ingredients (MAP, Alamin, Sorbitol, Methyl and Propyl Paraben) were blended and dispersed the maltitol syrup and Xanthan gum solution. The GMS and Glycerol were heated to about 80° C. (until molten), the medium chain triglycerides were added and heating maintained until the mixture was lump-free. The aqueous phase was heated to about 70° C., the oil phase was added to aqueous phase with continuous stirring. The Peppermint Oil was added, the mixture heated to 90° C. (held for 5 minutes) and then homogenised (Ultraturrex). The mixture was hot filled into a clean sterile bottle, rinsed with 96% ethanol and stored at 5° C. until required by patients.

The patients found that the emulsion provided a good coating on the inside of their mouth and provided good wetting.

Example 11

*Candida albicans* Adhesion Assay

A. Method

*Candida albicans* ATCC 10261 was grown in GSB medium (glucose, salts, biotin, Cannon et al, 1995) and radiolabelled with [$^{35}$S]methionine. Hydroxyapatite beads (20 mg, Biorad) were hydrated in KCl buffer (Cannon et al., 1995) and then incubated with pooled human saliva (30% v/v KCl buffer). The beads were washed with KCL buffer and then the saliva-coated hydroxyapatite beads were incubated with radiolabelled *C. albicans* cells. Non-adherent *C. albicans* cells were removed from the beads by washing with KCl buffer and then the percentage of the cells added to each assay that adhered to the SHA beads was calculated.

MAP 111 protein (DH 5.0, 140 μmol cross-links/g protein) was added at the following concentrations: 0.1%, 1.0% and 10.0% (in KCl buffer). The effect of the MAP protein on adhesion, relative to assays containing no MAP protein was calculated.

Each assay was conducted in triplicate and each experiment was conducted three times.

B. Results

Figure 13:
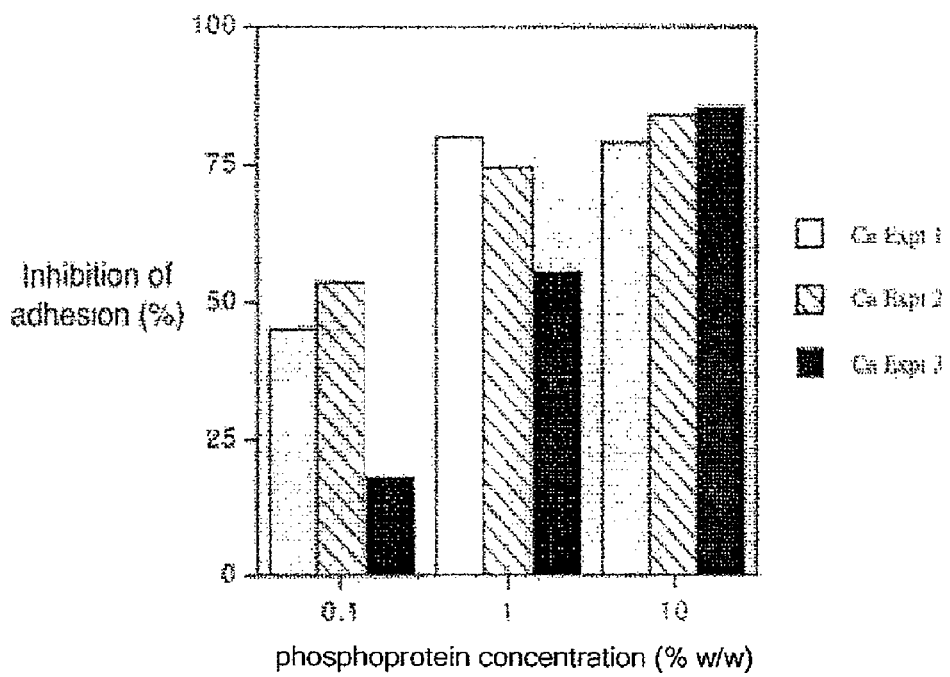
FIG. 13 shows the effect of MAP phosphoprotein concentration on the percent of *C. albicans* inhibited from adhering to hydroxyapatite beads over three experiments.

It can be seen from FIG. 13 that the protein inhibited adhesion of *Candida albicans* at concentrations as low 0.1%. The inhibition appears to dose-dependent.

Reference:

Cannon, R. D., Nand, A. K. and Jenkinson, H. F. (1995) Adherence of *Candida albicans* to human salivary components adsorbed to hydroxapatite. Microbiology 141:213-219

Example 12

Determination of Degree of Cross Linking Using High Performance Liquid Chromatography The following method was used to determine the degree of cross linking of the phosphoprotein preparations, in terms of the number of glutamyl/lysl bonds.

Chemicals and Reagents

ε-(γ-Glutamyl)lysine (G-L) and trifluoroacetic acid (TFA, protein sequencing grade), Prolidase (porcine kidney), Leucine aminopeptidase and cytosol from hog kidney, Carboxypeptidase A (bovine pancreas) and Pronase (*Streptomyces griseus*) and TRIS [Tris(hydroxymethyl)aminomethane] were purchased from Sigma Chem. Co. (Sydney, Australia). Acetonitrile (HPLC grade) was purchased from Biolab (Christchurch, New Zealand).

Proteolytic Digestion of the Cross-linked Proteins

A 48-50 mg aliquot of protein sample was weighed in a glass test tube (total volume 15 mL). A crystal of thymol and 2 ml of 0.2 M Tris (pH 8.0, HCl) was added, the solution vortexed and then incubated at 40° C. for 1 h to allow the dispersion of the protein. An aliquot of Pronase (0.4 U/mg protein) was added to the mixture which was then incubated at 37° C. for 24 h. The pronase digestion was continued for a further 24 h by the addition of another equal sized aliquot of pronase. After inactivation of pronase by heating at 100° C. (waterbath) for 10 min, the digestion was continued adding leucine aminopeptidase (0.4 U/mg protein), the solution being treated as for the pronase incubation. The digestion was continued using prolidase (0.45 U/mg protein) and then carboxypeptidase A (0.2 U/mg protein). After final inactivation the mixture was diluted to 7.5 g with ultrapure water (MilliQ water purification system)(Millipore, North Ryde, Australia).

HPLC Analysis of G-L

The HPLC system consisted of a Dionex GP40 gradient pump solvent delivery system connected to an ICI Instruments 1210 UV/Vis detector. Data was captured via an ITNS Acquisition Board and analysed using the AZUR chromatography software Version 1.1. The samples (100 μl) were separated on an Inertsil ODS-2 column (5 μm, 150×7.6 mm) (Phenomenex, Aucldand, New Zealand) connected to a guard column ($C_{18}$ ODS, 4 mm×3.0 mm ID)(Phenomenex) and a 2 μm prefilter. Analysis was performed at 2.5° C. The mobile phases were 0.1% TFA (v/v)(solvent A) and acetonitrile containing 0.1% TFA (v/v) (solvent B). The solvent program was as follows: 100% solvent A for 20 min, 0% to 100% solvent B from 20 to 25 min, 100% solvent B from 25 to 50 min. The detector wavelength was set at 210 nm and the flow rate was 1.0 ml/min.

All samples from proteolytic digestion were filtered on a 0.45 μm Millex-HA Millipore filter unit. 200 μl of sample was mixed with 100 μl of distilled water and 100 μl TFA (2% w/w). The G-L peak was identified by comparison to elution time of a standard and confirmed by standard addition of a G-L standard solution to the sample.

Example 13

Method of Determining Degree of Hydrolysis of Partially Hydrolysed Casein

Samples were prepared as either 0.1% or 1% protein (w/v) solutions in distilled water. A 100 μl aliquot of sample was added to 800 μl of 0.2125 M sodium phosphate buffer, pH 8.20. To this 800 μl 0.1% TNBS reagent was added, and the reagents were mixed well, wrapped in foil and incubated at 50° C. in a covered water-bath. After exactly 60 minutes the reaction was terminated by the addition of 1600 μl of 100 mM HCl and the samples left to cool to room temperature for 30 minutes before reading absorbance against a buffer/TNBS blank at 340 ηm.

INDUSTRIAL APPLICATION

It is believed that the methods and compositions of the present invention will find application in delivering bioactive metal ions, such as calcium and iron, to mammals. The invention is also expected to find particular application in compositions for remineralising teeth and/or for preventing or treating dental caries, tooth erosion, dentinal sensitivity or gingivitis.

The present invention is believed to possess certain advantages over teeth remineralising/anticaries compositions comprising phosphopeptides obtained from partial hydrolysis of casein, such as those described in U.S. Pat. No. 5,015,628. In particular, the phosphoprotein preparations used in the present invention have a clean flavour, in contrast to partial casein hydrolysates, which contain bitter-tasting hydrophobic peptides that need to be removed in order for the product to have an acceptable flavour. In addition, the phosphoprotein preparations of the present invention utilize the vast majority of the proteinaceous material from the casein (rather than just the proportion containing the casein phosphopeptides), thereby reducing wastage.

The phosphoprotein preparations used in the present invention also have advantages over remineralising/anticaries compositions containing unmodified casein or caseinate; in particular, the calcium-binding and teeth remineralising properties of the phosphoprotein preparations are, at least in preferred embodiments, believed to be significantly greater than those of casein. In addition, the phosphoprotein preparations are relatively soluble and have a lower viscosity than unmodified casein, thereby facilitating their incorporation into compositions.

Although the present invention has been described with reference to particular embodiments, those persons skilled in the art will appreciate that numerous variations and modifications may be made without departing from the scope of the invention as defined in the following claims.

The invention claimed is:

1. A composition for remineralizing tooth enamel and/or for treating or preventing one or more conditions selected from the group consisting of dental caries, tooth erosion, dentinal hypersensitivity and gingivitis in a mammal, wherein the composition comprises:

an effective amount of a phosphoprotein preparation in combination with one or more carriers or diluents, wherein the phosphoprotein preparation comprises a partially cross-linked partial hydrolysate of casein or a caseinate, wherein the partially cross-linked partial hydrolysate has been obtained by partially hydrolysing casein or a caseinate to a degree of hydrolysis of about 3% to about 8% of the total number of peptide bonds in the casein or caseinate, wherein the partially hydrolyzing step is followed by partially cross-linking the partially hydrolysed casein or caseinate to produce a phosphoprotein preparation having a degree of cross-linking of between 10 μmol and 250 μmol cross-links per gram of the total phosphoprotein in the preparation;

a source of calcium ions; and a source of phosphate ions, or a source of strontium ions.

2. A composition according to claim 1, wherein the partial hydrolysate has been obtained by enzymatic hydrolysis of acid casein, rennet casein or a caseinate.

3. A composition according to claim 2, wherein the enzyme is trypsin.

4. A composition according to claim 1, wherein the degree of hydrolysis is in the range of about 3.5% to about 7% of the total number of peptide bonds in the casein or caseinate.

5. A composition according to claim 1, wherein the degree of hydrolysis is in the range of about 4% to about 6.5% of the total number of peptide bonds in the casein or caseinate.

6. A composition according to claim 1, wherein the partial hydrolysate has been partially cross linked enzymatically, using the enzyme transglutaminase.

7. A composition according to claim 1, wherein the degree of partial cross linking is such that the resulting phosphoprotein preparation comprises between about 50 and about 160 μmol cross links per gram of total phosphoprotein in the preparation.

8. A composition according to claim 1, including a source of calcium ions and a source of phosphate ions.

9. A composition according to claim 8, wherein the molar ratio of calcium ions to phosphate ions is in the range of 0.8-1.2:0.4-0.8.

10. A composition according to claim 9, wherein the molar ratio of calcium ions to phosphate ions is about 1:0.6.

11. A composition according to claim 1, wherein the composition further comprises calcium phosphate.

12. A composition according to claim 1, wherein the composition includes calcium from natural milk.

13. A composition according to claim 1, wherein the composition includes a source of strontium ions.

14. A composition according to claim 13, wherein the composition further comprises a source of fluoride ions.

15. A composition according to claim 1, wherein the composition comprises a composition selected from the group consisting of a mouthwash, a dentifrice, toothpaste, a powder, an emulsion and a gel.

16. A composition according to claim 1, wherein the composition comprises an emulsion, wherein the phosphoprotein preparation is present in an amount of about 1% to about 15% by weight of the emulsion, and the emulsion further comprises natural milk calcium phosphate, in an amount of about 3% to about 12% by weight of the emulsion.

17. A composition according to claim 1, wherein the composition comprises a foodstuff and a confection.

* * * * *